United States Patent
Gilbertson

(10) Patent No.: US 6,893,637 B1
(45) Date of Patent: *May 17, 2005

(54) METHOD OF TREATING FIBROSIS

(75) Inventor: Debra G. Gilbertson, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 476 days.

This patent is subject to a terminal disclaimer.

(21) Appl. No.: 09/695,121

(22) Filed: Oct. 23, 2000

Related U.S. Application Data

(60) Provisional application No. 60/161,653, filed on Oct. 21, 1999, provisional application No. 60/165,255, filed on Nov. 12, 1999, and provisional application No. 60/222,223, filed on Aug. 1, 2000.

(51) Int. Cl.[7] .............................................. A61K 39/395
(52) U.S. Cl. ................................ 424/133.1; 424/135.1; 424/139.1; 424/141.1; 530/351
(58) Field of Search ........................... 424/133.1, 135.1, 424/139.1, 141.1, 130.1; 530/351; 514/44, 2–4

(56) References Cited

U.S. PATENT DOCUMENTS

| | | | |
|---|---|---|---|
| 5,238,950 A | 8/1993 | Clader et al. ................ | 514/360 |
| 5,700,823 A | 12/1997 | Hirth et al. .................. | 514/380 |
| 6,455,283 B1 * | 9/2002 | Ferrara et al. ............. | 435/69.4 |

FOREIGN PATENT DOCUMENTS

| | | |
|---|---|---|
| WO | 99/47677 | 9/1999 |
| WO | 00/34474 | 6/2000 |
| WO | 00/59940 | 10/2000 |

OTHER PUBLICATIONS

M Clark, Immunology Today, "Antibody humanization: a case of the 'Emperor's new clothes'?" Aug. vol. 21, No. 8, pp. 397–402.*
Yu L. et al. Therapeutic stratagies to halt renal fibrosis. Current Opin. Pharm. 2002; 2:177–181.
Kitamura Y. et al. A loss–of–function mutation of c–kit results in depletion of mast cells andinterstitial cells of Cajal, while its gain–of–function mutation results in their oncogenesis. Mutation Research 2001; 477:165–171.
Dhanasekaran N. et al. Regulation of cell proliferation by G proteins. Oncogene 1989; 17:1383–1394.
Mann D.A. et al. Transcreiptional regulationof hepatic stellate cell activation (Gut 2002; 50:891–896).
Martinet et al., *New England Journal of Medicine* 317:202–209, 1987.
Deuel et al., *New England Journal of Medicine* 317:236, 1987.
Isaka et al., *J. Clin. Invest.* 92:2597–2601, 1993.
Yoshida et al., *Biochem. Biophys. Res. Comm.* 265: 503–508, 1999.
Johnson et al., *J. Exp. Med.* 175: 1413–1416, 1992.
Rice et al., Am. J. Path. 155: 213–221, 1999.
Yi et al., *Am. J. Path. 149*:539–548, 1996.
Floege et al., *J. Clin. Invest.* 92: 2952–2962, 1993.
Li et al., *Nature Cell Biol.* 2: 302–309, 2000.
Bergsten et al., *Nature Cell Biol.* 3: 512–516, 2001.
LaRochelle et al., *Nature Cell Biol.* 3: 517–521, 2001.
Uutela et al., *Circulation 103*: 2242–2247, 2001.
Johnson et al., *J. Exp. Med.* 175: 1413–1416, 1992.
Preaux et al., *Hepatology 26*: 315–322, 1997.
Kallio et al.,*Am. J. Respir. Crit. Care Med. 160*: 1324–1332, 1999.
Yagi et al., *Gen. Pharmac. 31*: 765–773, 1998.
Pinzani et al., *Brit. J. Pharmac. 119*: 1117–1124, 1996.
Friedman, *Seminars in Liver Disease 19*: 129–140, 1999.
Li et al., *Journal of Gastroenterology and Hepatology 14*: 618–633, 1999.
Brady et al., *Biochem.Biophys. Res. Comm.248*: 174–179, 1998.
Heldin et al., *Physiological Reviews 79*: 1283–1316, 1999.
Isbrucker et al., *Tox. App. Pharmac. 149*: 120–126, 1998.

* cited by examiner

*Primary Examiner*—Dave Trong Nguyen
*Assistant Examiner*—Jon Eric Angell
(74) *Attorney, Agent, or Firm*—Gary E. Parker

(57) ABSTRACT

Materials and Methods for treating fibrosis in a mammal are disclosed. The methods comprise administering to a mammal a composition comprising a therapeutically effective amount of a zvegf3 antagonist in combination with a pharmaceutically acceptable delivery vehicle. Zvegf3 antagonists include anti-zvegf3 antibodies, mitogenically inactive receptor-binding zvegf3 variant polypeptides, and inhibitory polynucleotides. Within one embodiment of the fibrosis is liver fibrosis.

20 Claims, 8 Drawing Sheets

Figure 1A:
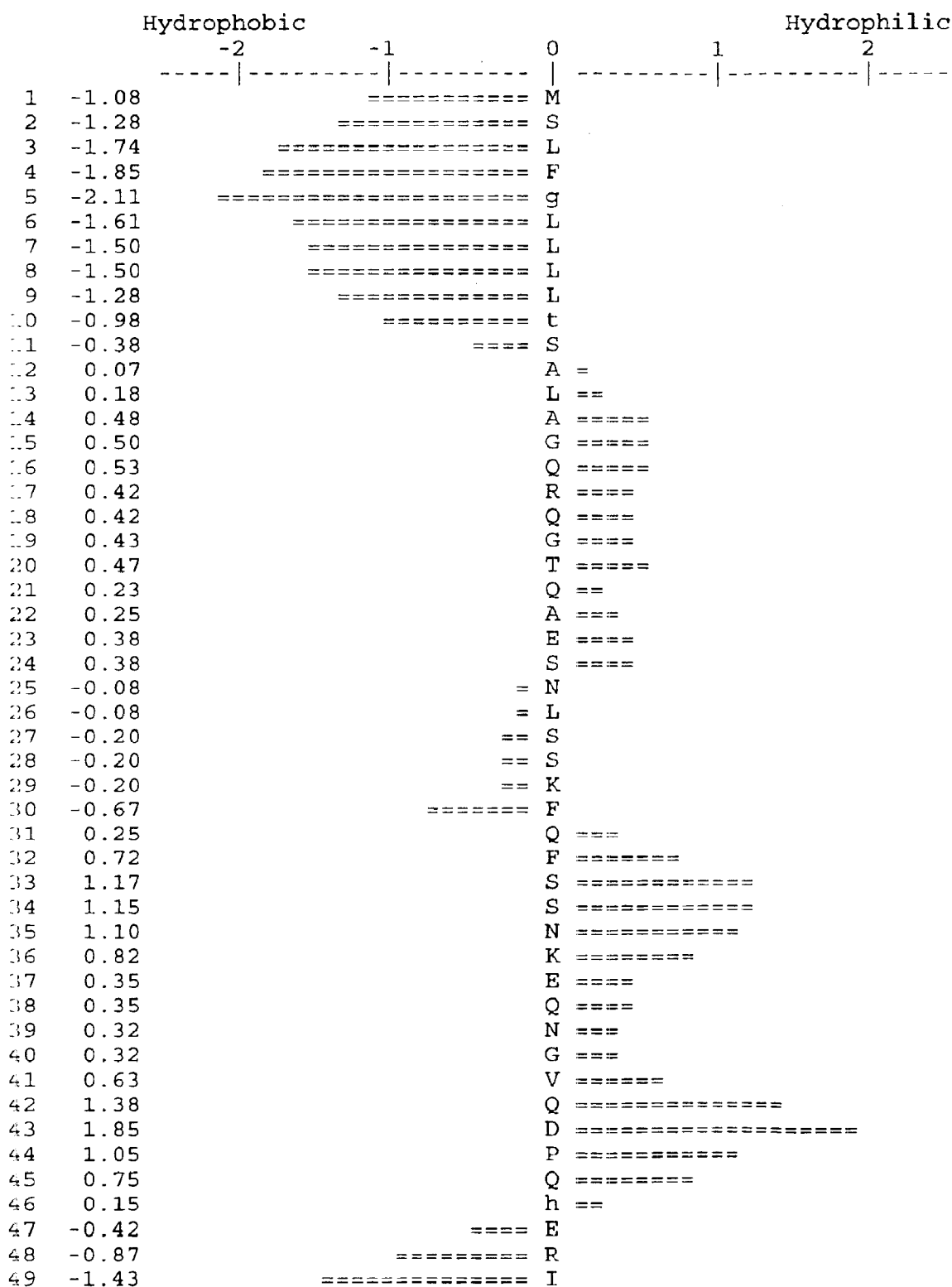

| | | | |
|---|---|---|---|
| 265 | 0.15 | | R = |
| 266 | -0.92 | ========= | T |
| 267 | -0.85 | ========= | D |
| 268 | -1.35 | ============= | T |
| 269 | -1.45 | =============== | I |
| 270 | -1.45 | ============== | F |
| 271 | -1.33 | ============ | W |
| 272 | -1.02 | ========== | P |
| 273 | -0.52 | ===== | G |
| 274 | -0.02 | | C |
| 275 | -0.02 | | L |
| 276 | 0.28 | | L === |
| 277 | 0.58 | | V ====== |
| 278 | 0.87 | | K ======== |
| 279 | 0.20 | | R == |
| 280 | -0.38 | ==== | C |
| 281 | -0.38 | ==== | G |
| 282 | -0.55 | ====== | G |
| 283 | -0.85 | ========= | N |
| 284 | -0.97 | ========== | C |
| 285 | -0.77 | ======== | A |
| 286 | -0.85 | ========= | C |
| 287 | -0.65 | ======= | C |
| 288 | 0.02 | | L |
| 289 | 0.15 | | H == |
| 290 | 0.27 | | N === |
| 291 | 0.07 | | C = |
| 292 | -0.02 | | N |
| 293 | -0.05 | | E |
| 294 | -0.50 | ===== | C |
| 295 | 0.17 | | Q == |
| 296 | -0.12 | = | C |
| 297 | -0.02 | | V |
| 298 | 0.73 | | P ======= |
| 299 | 1.23 | | S ============ |
| 300 | 1.20 | | K =========== |
| 301 | 0.62 | | V ====== |
| 302 | 1.37 | | T ============== |
| 303 | 1.18 | | K ============ |
| 304 | 0.38 | | K ==== |
| 305 | -0.08 | = | Y |
| 306 | -0.40 | ==== | H |
| 307 | 0.18 | | E == |
| 308 | -0.32 | === | V |
| 309 | 0.43 | | L ==== |
| 310 | 0.67 | | Q ======= |
| 311 | 0.63 | | L ====== |
| 312 | 0.68 | | R ======= |
| 313 | 0.68 | | P ======= |
| 314 | 0.68 | | K ======= |
| 315 | -0.12 | = | T |
| 316 | -0.13 | = | G |
| 317 | 0.37 | | V ==== |
| 318 | 0.67 | | R ======= |

Fig. 1F

```
MSLFGLLLLLTSALAGQRQGTQAESNLSSKFQFSSNKEQNGVQDPQHERIITVSTNGSIHS

MLLLGLLLLLTSALAGQRTGTRAESNLSSKLQLSSDKEQNGVQDPRHERVVTISGNGSIHS
         10        20        30        40        50        60

PRFPHTYPRNTVLVWRLVAVEENVWIQLTFDERFGLEDPEDDICKYDFVEVEEPSDGTIL

PKFPHTYPRNMVLVWRLVAVDENVRIQLTFDERFGLEDPEDDICKYDFVEVEEPSDGSVL
         70        80        90       100       110       120

GRWCGSGTVPGKQISKGNQIRIRFVSDEYFPSEPGFCIHYNIVMPQFTEAVSPSVLPPSA

GRWCGSGTVPGKQTSKGNHIRIRFVSDEYFPSEPGFCIHYSIIMPQVTETTSPSVLPPSS
        130       140       150       160       170       180

LPLDLLNNAITAFSTLEDLIRYLEPERWQLDLEDLYRPTWQLLGKAFVFGRKSRVVDLNL

LSLDLLNNAVTAFSTLEELIRYLEPDRWQVDLDSLYKPTWQLLGKAFLYGKKSKVVNLNL
        190       200       210       220       230       240

LTEEVRLYSCTPRNFSVSIREELKRTDTIFWPGCLLVKRCGGNCACCLHNCNECQCVPSK

LKEEVKLYSCTPRNFSVSIREELKRTDTIFWPGCLLVKRCGGNCACCLHNCNECQCVPRK
        250       260       270       280       290       300

VTKKYHEVLQLRPKTGVRGLHKSLTDVALEHHEECDCVCRGSTGG (SEQ ID NO:2)

VTKKYHEVLQLRPKTGVKGLHKSLTDVALEHHEECDCVCRGNAGG (SEQ ID NO:4)
        310       320       330       340
```

Fig. 2

SEQUENCE LISTING

<160> NUMBER OF SEQ ID NOS: 18

<210> SEQ ID NO 1
<211> LENGTH: 1760
<212> TYPE: DNA
<213> ORGANISM: Homo sapiens
<220> FEATURE:
<221> NAME/KEY: CDS
<222> LOCATION: (154)...(1191)

<400> SEQUENCE: 1

```
attatgtgga aactaccctg cgattctctg ctgccagagc aggctcggcg cttccacccc         60
agtgcagcct tccctggcg gtggtgaaag agactcggga gtcgctgctt ccaaagtgcc        120
cgccgtgagt gagctctcac cccagtcagc caa atg agc ctc ttc ggg ctt ctc        174
                                    Met Ser Leu Phe Gly Leu Leu
                                     1               5 ctg ctg aca tct gcc ctg gcc ggc cag aga cag ggg act cag gcg gaa          222
Leu Leu Thr Ser Ala Leu Ala Gly Gln Arg Gln Gly Thr Gln Ala Glu
         10                  15                  20 tcc aac ctg agt agt aaa ttc cag ttt tcc agc aac aag gaa cag aac          270
Ser Asn Leu Ser Ser Lys Phe Gln Phe Ser Ser Asn Lys Glu Gln Asn
     25                  30                  35 gga gta caa gat cct cag cat gag aga att att act gtg tct act aat          318
Gly Val Gln Asp Pro Gln His Glu Arg Ile Ile Thr Val Ser Thr Asn
 40                  45                  50                  55 gga agt att cac agc cca agg ttt cct cat act tat cca aga aat acg          366
Gly Ser Ile His Ser Pro Arg Phe Pro His Thr Tyr Pro Arg Asn Thr
                 60                  65                  70 gtc ttg gta tgg aga tta gta gca gta gag gaa aat gta tgg ata caa          414
Val Leu Val Trp Arg Leu Val Ala Val Glu Glu Asn Val Trp Ile Gln
             75                  80                  85 ctt acg ttt gat gaa aga ttt ggg ctt gaa gac cca gaa gat gac ata          462
```

-continued

```
                Leu Thr Phe Asp Glu Arg Phe Gly Leu Glu Asp Pro Glu Asp Ile
                         90                  95                 100 tgc aag tat gat ttt gta gaa gtt gag gaa ccc agt gat gga act ata        510
Cys Lys Tyr Asp Phe Val Glu Val Glu Glu Pro Ser Asp Gly Thr Ile
    105                 110                 115 tta ggg cgc tgg tgt ggt tct ggt act gta cca gga aaa cag att tct        558
Leu Gly Arg Trp Cys Gly Ser Gly Thr Val Pro Gly Lys Gln Ile Ser
120                 125                 130                 135 aaa gga aat caa att agg ata aga ttt gta tct gat gaa tat ttt cct        606
Lys Gly Asn Gln Ile Arg Ile Arg Phe Val Ser Asp Glu Tyr Phe Pro
                140                 145                 150 tct gaa cca ggg ttc tgc atc cac tac aac att gtc atg cca caa ttc        654
Ser Glu Pro Gly Phe Cys Ile His Tyr Asn Ile Val Met Pro Gln Phe
            155                 160                 165 aca gaa gct gtg agt cct tca gtg cta ccc cct tca gct ttg cca ctg        702
Thr Glu Ala Val Ser Pro Ser Val Leu Pro Pro Ser Ala Leu Pro Leu
        170                 175                 180 gac ctg ctt aat aat gct ata act gcc ttt agt acc ttg gaa gac ctt        750
Asp Leu Leu Asn Asn Ala Ile Thr Ala Phe Ser Thr Leu Glu Asp Leu
    185                 190                 195 att cga tat ctt gaa cca gag aga tgg cag ttg gac tta gaa gat cta        798
Ile Arg Tyr Leu Glu Pro Glu Arg Trp Gln Leu Asp Leu Glu Asp Leu
200                 205                 210                 215 tat agg cca act tgg caa ctt ctt ggc aag gct ttt gtt ttt gga aga        846
Tyr Arg Pro Thr Trp Gln Leu Leu Gly Lys Ala Phe Val Phe Gly Arg
                220                 225                 230 aaa tcc aga gtg gtg gat ctg aac ctt cta aca gag gag gta aga tta        894
Lys Ser Arg Val Val Asp Leu Asn Leu Leu Thr Glu Glu Val Arg Leu
            235                 240                 245 tac agc tgc aca cct cgt aac ttc tca gtg tcc ata agg gaa gaa cta        942
Tyr Ser Cys Thr Pro Arg Asn Phe Ser Val Ser Ile Arg Glu Glu Leu
        250                 255                 260 aag aga acc gat acc att ttc tgg cca ggt tgt ctc ctg gtt aaa cgc        990
Lys Arg Thr Asp Thr Ile Phe Trp Pro Gly Cys Leu Leu Val Lys Arg
    265                 270                 275 tgt ggt ggg aac tgt gcc tgt tgt ctc cac aat tgc aat gaa tgt caa       1038
Cys Gly Gly Asn Cys Ala Cys Cys Leu His Asn Cys Asn Glu Cys Gln
280                 285                 290                 295 tgt gtc cca agc aaa gtt act aaa aaa tac cac gag gtc ctt cag ttg       1086
Cys Val Pro Ser Lys Val Thr Lys Lys Tyr His Glu Val Leu Gln Leu
                300                 305                 310 aga cca aag acc ggt gtc agg gga ttg cac aaa tca ctc acc gac gtg       1134
Arg Pro Lys Thr Gly Val Arg Gly Leu His Lys Ser Leu Thr Asp Val
            315                 320                 325 gcc ctg gag cac cat gag gag tgt gac tgt gtg tgc aga ggg agc aca       1182
Ala Leu Glu His His Glu Glu Cys Asp Cys Val Cys Arg Gly Ser Thr
        330                 335                 340 gga gga tag ccgcatcacc accagcagct cttgcccaga gctgtgcagt               1231
Gly Gly *
    345 gcagtggctg attctattag agaacgtatg cgttatctcc atccttaatc tcagttgttt     1291 gcttcaagga cctttcatct tcaggattta cagtgcattc tgaaagagga gacatcaaac     1351 agaattagga gttgtgcaac agctcttttg agaggaggcc taaggacag gagaaaaggt      1411 cttcaatcgt ggaaagaaaa ttaaatgttg tattaaatag atcaccagct agtttcagag     1471 ttaccatgta cgtattccac tagctgggtt ctgtatttca gttctttcga tacggcttag    1531 ggtaatgtca gtacaggaaa aaaactgtgc aagtgagcac ctgattccgt tgccttgctt    1591
```
aactctaaag ctccatgtcc tgggcctaaa atcgtataaa atctggattt tttttttttt    1651
tttttgctca tattcacata tgtaaaccag aacattctat gtactacaaa cctggttttt    1711
aaaaaggaac tatgttgcta tgaattaaac ttgtgtcgtg ctgatagga               1760

<210> SEQ ID NO 2
<211> LENGTH: 345
<212> TYPE: PRT
<213> ORGANISM: Homo sapiens

<400> SEQUENCE: 2

Met Ser Leu Phe Gly Leu Leu Leu Thr Ser Ala Leu Ala Gly Gln
  1               5                  10                  15

Arg Gln Gly Thr Gln Ala Glu Ser Asn Leu Ser Ser Lys Phe Gln Phe
                 20                  25                  30

Ser Ser Asn Lys Glu Gln Asn Gly Val Gln Asp Pro Gln His Glu Arg
             35                  40                  45

Ile Ile Thr Val Ser Thr Asn Gly Ser Ile His Ser Pro Arg Phe Pro
 50                  55                  60

His Thr Tyr Pro Arg Asn Thr Val Leu Val Trp Arg Leu Val Ala Val
 65                  70                  75                  80

Glu Glu Asn Val Trp Ile Gln Leu Thr Phe Asp Glu Arg Phe Gly Leu
                 85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345

```
<210> SEQ ID NO 3
<211> LENGTH: 3571
<212> TYPE: DNA
<213> ORGANISM: Mus musculus
<220> FEATURE:
<221> NAME/KEY: CDS
<222> LOCATION: (1049)...(2086)

<400> SEQUENCE: 3
gaattcccgg gtcgacccac gcgtccgggc gcccagggga aaggaagctg ggggccgcct      60
ggcggcattc ctcgccgcag tgtgggctcc gtctgccgcg gggcccgcag tgcccctgt     120 ctgcgccagc acctgttggc ccgccagctg gccgcccgcg ccccccgcgc ccccgcgcc     180 cgcccggccg ccagccccgc gccccgcgcg ccgcccgctg ggggaaagtg gagacgggga     240
ggggacaaga gcgatcctcc aggccagcca ggccttccct tagccgcccg tgcttagccg     300
ccacctctcc tcagccctgc gtcctgccct gccttagggc aggcatccga gcgctcgcga     360
ctccgagccg cccaagctct cccggcttcc cgcagcactt cgccggtacc cgagggaact     420
tcggtggcca ccgactgcag caaggaggag gctccgcggt ggatccgggc cagtcccgag     480
tcgtccccgc ggcctctctg cccgcccggg accgcgcgg cactcgcagg gcacggtccc     540 ctcccccag gtgggggtgg ggcgccgcct gccgccccga tcagcagctt tgtcattgat     600
cccaaggtgc tcgcctcgct gccgacctgg cttccagtct ggcttggcgg gaccccgagt     660
cctcgcctgt gtcctgtccc ccaaactgac aggtgctccc tgcgagtcgc cacgactcat     720
cgccgctccc ccgcgtcccc acccttctt tcctccctcg cctaccccca ccccccgcac     780
ttcggcacag ctcaggattt gtttaaacct tgggaaactg gttcaggtcc aggttttgct     840
ttgatccttt tcaaaaactg gagacacaga agagggctct aggaaaaact tttggatggg     900
attatgtgga aactaccctg cgattctctg ctgccagagc cggccaggcg cttccaccgc     960
agcgcagcct ttccccggct gggctgagcc ttggagtcgt cgcttcccca gtgcccgccg    1020
cgagtgagcc ctcgccccag tcagccaa atg ctc ctc ctc ggc ctc ctc ctg      1072
                                Met Leu Leu Leu Gly Leu Leu Leu
                                 1               5 ctg aca tct gcc ctg gcc ggc caa aga acg ggg act cgg gct gag tcc      1120
Leu Thr Ser Ala Leu Ala Gly Gln Arg Thr Gly Thr Arg Ala Glu Ser
        10                  15                  20 aac ctg agc agc aag ttg cag ctc tcc agc gac aag gaa cag aac gga      1168
Asn Leu Ser Ser Lys Leu Gln Leu Ser Ser Asp Lys Glu Gln Asn Gly
 25                  30                  35                  40 gtg caa gat ccc cgg cat gag aga gtt gtc act ata tct ggt aat ggg      1216
Val Gln Asp Pro Arg His Glu Arg Val Val Thr Ile Ser Gly Asn Gly
                 45                  50                  55 agc atc cac agc ccg aag ttt cct cat aca tac cca aga aat atg gtg      1264
Ser Ile His Ser Pro Lys Phe Pro His Thr Tyr Pro Arg Asn Met Val
             60                  65                  70 ctg gtg tgg aga tta gtt gca gta gat gaa aat gtg cgg atc cag ctg      1312
Leu Val Trp Arg Leu Val Ala Val Asp Glu Asn Val Arg Ile Gln Leu
         75                  80                  85 aca ttt gat gag aga ttt ggg ctg gaa gat cca gaa gac gat ata tgc      1360
Thr Phe Asp Glu Arg Phe Gly Leu Glu Asp Pro Glu Asp Asp Ile Cys
     90                  95                 100 aag tat gat ttt gta gaa gtt gag gag ccc agt gat gga agt gtt tta      1408
Lys Tyr Asp Phe Val Glu Val Glu Glu Pro Ser Asp Gly Ser Val Leu
105                 110                 115                 120 gga cgc tgg tgt ggt tct ggg act gtg cca gga aag cag act tct aaa      1456
```

```
Gly Arg Trp Cys Gly Ser Gly Thr Val Pro Gly Lys Gln Thr Ser Lys
                125                 130                 135 gga aat cat atc agg ata aga ttt gta tct gat gag tat ttt cca tct    1504
Gly Asn His Ile Arg Ile Arg Phe Val Ser Asp Glu Tyr Phe Pro Ser
            140                 145                 150 gaa ccc gga ttc tgc atc cac tac agt att atc atg cca caa gtc aca    1552
Glu Pro Gly Phe Cys Ile His Tyr Ser Ile Ile Met Pro Gln Val Thr
        155                 160                 165 gaa acc acg agt cct tcg gtg ttg ccc cct tca tct ttg tca ttg gac    1600
Glu Thr Thr Ser Pro Ser Val Leu Pro Pro Ser Ser Leu Ser Leu Asp
    170                 175                 180 ctg ctc aac aat gct gtg act gcc ttc agt acc ttg gaa gag ctg att    1648
Leu Leu Asn Asn Ala Val Thr Ala Phe Ser Thr Leu Glu Glu Leu Ile
185                 190                 195                 200 cgg tac cta gag cca gat cga tgg cag gtg gac ttg gac agc ctc tac    1696
Arg Tyr Leu Glu Pro Asp Arg Trp Gln Val Asp Leu Asp Ser Leu Tyr
                205                 210                 215 aag cca aca tgg cag ctt ttg ggc aag gct ttc ctg tat ggg aaa aaa    1744
Lys Pro Thr Trp Gln Leu Leu Gly Lys Ala Phe Leu Tyr Gly Lys Lys
            220                 225                 230 agc aaa gtg gtg aat ctg aat ctc ctc aag gaa gag gta aaa ctc tac    1792
Ser Lys Val Val Asn Leu Asn Leu Leu Lys Glu Glu Val Lys Leu Tyr
        235                 240                 245 agc tgc aca ccc cgg aac ttc tca gtg tcc ata cgg gaa gag cta aag    1840
Ser Cys Thr Pro Arg Asn Phe Ser Val Ser Ile Arg Glu Glu Leu Lys
    250                 255                 260 agg aca gat acc ata ttc tgg cca ggt tgt ctc ctg gtc aag cgc tgt    1888
Arg Thr Asp Thr Ile Phe Trp Pro Gly Cys Leu Leu Val Lys Arg Cys
265                 270                 275                 280 gga gga aat tgt gcc tgt tgt ctc cat aat tgc aat gaa tgt cag tgt    1936
Gly Gly Asn Cys Ala Cys Cys Leu His Asn Cys Asn Glu Cys Gln Cys
                285                 290                 295 gtc cca cgt aaa gtt aca aaa aag tac cat gag gtc ctt cag ttg aga    1984
Val Pro Arg Lys Val Thr Lys Lys Tyr His Glu Val Leu Gln Leu Arg
            300                 305                 310 cca aaa act gga gtc aag gga ttg cat aag tca ctc act gat gtg gct    2032
Pro Lys Thr Gly Val Lys Gly Leu His Lys Ser Leu Thr Asp Val Ala
        315                 320                 325 ctg gaa cac cac gag gaa tgt gac tgt gtg tgt aga gga aac gca gga    2080
Leu Glu His His Glu Glu Cys Asp Cys Val Cys Arg Gly Asn Ala Gly
    330                 335                 340 ggg taa ctgcagcctt cgtagcagca cacgtgagca ctggcattct gtgtaccccc    2136
Gly  *
345 acaagcaacc ttcatcccca ccagcgttgg ccgcagggct ctcagctgct gatgctggct    2196 atggtaaaga tcttactcgt ctccaaccaa attctcagtt gtttgcttca atagccttcc    2256 cctgcaggac ttcaagtgtc ttctaaaaga ccagaggcac caagaggagt caatcacaaa    2316 gcactgcctt ctagaggaag cccagacaat ggtcttctga ccacagaaac aaatgaaatg    2376 aatgtagatc gctagcaaac tctggagtga cagcatttct tttccactga cagaatggtg    2436 tagcttagtt gtcttgatat gggcaagtga tgtcagcaca agaaaatggt gaaaacaca    2496 cacttgattg tgaacaatgc agaaatactt ggatttctcc aacctgtttg catagataga    2556 cagatgctct gttttctaca aactcaaagc ttttagagag cagctatgtt aataggaatt    2616 aaatgtgcca tgctgaaagg aaagactgaa gttttcaatg cttggcaact tctccgcaat    2676 ttggaggaaa ggtgcggtca tggtttggag aaagcacacc tgcacagagg agtggccttc    2736
```

-continued

```
ccttcccttc cctctgaggt ggcttctgtg tttcattgtg tatatttta tattctcctt    2796
ttgacattat aactgttggc ttttctaatc ttgttaaata tttctatttt taccaaaggt   2856
atttaatatt cttttttatg acaacctaga gcaattattt ttagcttgat aattttttt    2916
tctaaacaaa attgttatag ccagaagaac aaagatgatt gatataaaaa tcttgttgct   2976
ctgacaaaaa catatgtatt tcttccttgt atggtgctag agcttagcgt catctgcatt   3036
tgaaaagatg gaatgggaa gttttagaa ttggtaggtc gcaggacag tttgataaca      3096
actgtactat catcaattcc caattctgtt cttagagcta cgaacagaac agagcttgag   3156
taaatatgga gccattgcta acctacccct ttctatggga ataggagta tagctcagag    3216
aagcacgtcc ccagaaacct cgaccatttc taggcacagt gttctgggct atgctgcgct   3276
gtatggacat atcctattta tttcaatact agggttttat tacctttaaa ctctgctcca   3336
tacacttgta ttaatacatg gatattttta tgtacagaag tatatcattt aaggagttca   3396
cttattatac tctttggcaa ttgcaaagaa aatcaacata atacattgct tgtaaatgct   3456
taatctgtgc ccaagttttg tggtgactat ttgaattaaa atgtattgaa tcatcaaata   3516
aaataatctg gctatttggg ggaaaaaaaa aaaaaaaaa aaaagggcg gccgc          3571
```

<210> SEQ ID NO 4
<211> LENGTH: 345
<212> TYPE: PRT
<213> ORGANISM: Mus musculus

<400> SEQUENCE: 4

```
Met Leu Leu Leu Gly Leu Leu Leu Thr Ser Ala Leu Ala Gly Gln
 1               5                  10                  15
Arg Thr Gly Thr Arg Ala Glu Ser Asn Leu Ser Lys Leu Gln Leu
            20                  25                  30
Ser Ser Asp Lys Glu Gln Asn Gly Val Gln Asp Pro Arg His Glu Arg
            35                  40                  45
Val Val Thr Ile Ser Gly Asn Gly Ser Ile His Ser Pro Lys Phe Pro
 50                  55                  60
His Thr Tyr Pro Arg Asn Met Val Leu Val Trp Arg Leu Val Ala Val
 65                  70                  75                  80
Asp Glu Asn Val Arg Ile Gln Leu Thr Phe Asp Glu Arg Phe Gly Leu
                85                  90                  95
Glu Asp Pro Glu Asp Asp Ile Cys Lys Tyr Asp Phe Val Glu Val Glu
            100                 105                 110
Glu Pro Ser Asp Gly Ser Val Leu Gly Arg Trp Cys Gly Ser Gly Thr
            115                 120                 125
Val Pro Gly Lys Gln Thr Ser Lys Gly Asn His Ile Arg Ile Arg Phe
            130                 135                 140
Val Ser Asp Glu Tyr Phe Pro Ser Glu Pro Gly Phe Cys Ile His Tyr
145                 150                 155                 160
Ser Ile Ile Met Pro Gln Val Thr Glu Thr Thr Ser Pro Ser Val Leu
                165                 170                 175
Pro Pro Ser Ser Leu Ser Leu Asp Leu Leu Asn Asn Ala Val Thr Ala
            180                 185                 190
Phe Ser Thr Leu Glu Glu Leu Ile Arg Tyr Leu Glu Pro Asp Arg Trp
            195                 200                 205
Gln Val Asp Leu Asp Ser Leu Tyr Lys Pro Thr Trp Gln Leu Leu Gly
            210                 215                 220
Lys Ala Phe Leu Tyr Gly Lys Lys Ser Lys Val Val Asn Leu Asn Leu
```

```
                225                 230                 235                 240
Leu Lys Glu Glu Val Lys Leu Tyr Ser Cys Thr Pro Arg Asn Phe Ser
                    245                 250                 255

Val Ser Ile Arg Glu Glu Leu Lys Arg Thr Asp Thr Ile Phe Trp Pro
                260                 265                 270

Gly Cys Leu Leu Val Lys Arg Cys Gly Gly Asn Cys Ala Cys Cys Leu
            275                 280                 285

His Asn Cys Asn Glu Cys Gln Cys Val Pro Arg Lys Val Thr Lys Lys
        290                 295                 300

Tyr His Glu Val Leu Gln Leu Arg Pro Lys Thr Gly Val Lys Gly Leu
305                 310                 315                 320

His Lys Ser Leu Thr Asp Val Ala Leu Glu His His Glu Glu Cys Asp
                325                 330                 335

Cys Val Cys Arg Gly Asn Ala Gly Gly
                340                 345

<210> SEQ ID NO 5
<211> LENGTH: 370
<212> TYPE: PRT
<213> ORGANISM: Homo sapiens

<400> SEQUENCE: 5

Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
                20                  25                  30

Leu Arg Asn Ala Asn Leu Arg Arg Asp Glu Ser Asn His Leu Thr Asp
            35                  40                  45

Leu Tyr Arg Arg Asp Glu Thr Ile Gln Val Lys Gly Asn Gly Tyr Val
        50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
                100                 105                 110

Phe Val Glu Val Glu Asp Ile Ser Glu Thr Ser Thr Ile Ile Arg Gly
            115                 120                 125

Arg Trp Cys Gly His Lys Glu Val Pro Pro Arg Ile Lys Ser Arg Thr
        130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255
```

```
Lys Val Asp Leu Asp Arg Leu Asn Asp Asp Ala Lys Arg Tyr Ser Cys
             260                 265                 270

Thr Pro Arg Asn Tyr Ser Val Asn Ile Arg Glu Glu Leu Lys Leu Ala
         275                 280                 285

Asn Val Val Phe Phe Pro Arg Cys Leu Leu Val Gln Arg Cys Gly Gly
         290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
             325                 330                 335

His Ile Lys Arg Arg Gly Arg Ala Lys Thr Met Ala Leu Val Asp Ile
             340                 345                 350

Gln Leu Asp His His Glu Arg Cys Asp Cys Ile Cys Ser Ser Arg Pro
         355                 360                 365

Pro Arg
    370
```

<210> SEQ ID NO 6
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 6
agcaggtcca gtggcaaagc                                          20

<210> SEQ ID NO 7
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 7
cgtttgatga agatttgggc                                          21

<210> SEQ ID NO 8
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 8
ggaggtctat ataagcagag c                                        21

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 9
tgagccctcg ccccagtcag                                          20

<210> SEQ ID NO 10
<211> LENGTH: 25
<212> TYPE: DNA
<213> ORGANISM: Artificial Sequence
<220> FEATURE:
<223> OTHER INFORMATION: oligonucleotide primer

```
<400> SEQUENCE: 10
acatacagga aagccttgcc caaaa                                              25

<210> SEQ ID NO 11
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 11
aaactaccct gcgattctct gctgc                                              25

<210> SEQ ID NO 12
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 12
ggtaaatgga gcttggctga g                                                  21

<210> SEQ ID NO 13
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 13
tctggacgtc ctcctgctgg tatag                                              25

<210> SEQ ID NO 14
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 14
ggtatggagc cagggggcaag ttggg                                             25

<210> SEQ ID NO 15
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 15
gagtggcaac ttccagggcc aggagag                                            27

<210> SEQ ID NO 16
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 16
cttttgctag cctcaaccct gactatc                                            27

<210> SEQ ID NO 17
```

-continued

```
<211> LENGTH: 35
<212> TYPE: DNA
<213> ORGANISM: Artificial Sequence
<220> FEATURE:
<223> OTHER INFORMATION: oligonucleotide primer ZC20,180

<400> SEQUENCE: 17
cgcgcggttt aaacgccacc atgagcctct tcggg                              35

<210> SEQ ID NO 18
<211> LENGTH: 32
<212> TYPE: DNA
<213> ORGANISM: Artificial Sequence
<220> FEATURE:
<223> OTHER INFORMATION: oligonucleotide primer ZC20,181

<400> SEQUENCE: 18
cgtatcggcg cgccctatcc tcctgtgctc cc                                 32
```

US 6,893,637 B1

METHOD OF TREATING FIBROSIS

CROSS-REFERENCE TO RELATED APPLICATIONS

This application claims priority under 35 U.S.C. 119(e) from U.S. provisional applications Ser. Nos. 60/161,653, filed Oct. 21, 1999; 60/165,255, filed Nov. 12, 1999; and 60/222,223, filed Aug. 1, 2000.

BACKGROUND OF THE INVENTION

Fibrosis is the abnormal accumulation of fibrous tissue that can occur as a part of the wound-healing process in damaged tissue. Such tissue damage may result from physical injury, inflammation, infection, exposure to toxins, and other causes. Examples of fibrosis include dermal scar formation, keloids, liver fibrosis, lung fibrosis (e.g., silicosis, asbestosis), kidney fibrosis (including diabetic nephropathy), and glomerulosclerosis.

Liver (hepatic) fibrosis, for example, occurs as a part of the wound-healing response to chronic liver injury. Fibrosis occurs as a complication of haemochromatosis, Wilson's disease, alcoholism, schistosomiasis, viral hepatitis, bile duct obstruction, exposure to toxins, and metabolic disorders. This formation of scar tissue is believed to represent an attempt by the body to encapsulate the injured tissue. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death.

In recent years there have been significant advances in the understanding of the cellular and biochemical mechanisms underlying liver fibrosis (reviewed by Li and Friedman, *J. Gastroenterol. Hepatol.* 14:618–633, 1999). Stellate cells are believed to be a major source of extracellular matrix in the liver. Stellate cells respond to a variety of cytokines present in the liver, some of which they also produce (Friedman, *Seminars in Liver Disease* 19:129–140, 1999).

As summarized by Li and Friedman (ibid.), actual and proposed therapeutic strategies for liver fibrosis include removal of the underlying cause (e.g., toxin or infectious agent), suppression of inflammation (using, e.g., corticosteroids, IL-1 receptor antagonists, or other agents), down-regulation of stellate cell activation using, e.g., gamma interferon or antioxidants), promotion of matrix degradation, or promotion of stellate cell apoptosis. Despite recent progress, many of these strategies are still in the experimental stage, and existing therapies are aimed at suppressing inflammation rather than addressing the underlying biochemical processes. Thus, there remains a need in the art for materials and methods for treating fibrosis, including liver fibrosis.

DESCRIPTION OF THE INVENTION

The present invention provides materials and methods for reducing cell proliferation or extracellular matrix production, treating fibrosis, and reducing stellate cell activation in a mammal.

Within one aspect of the invention there is provided a method of reducing cell proliferation or extracellular matrix production in a mammal comprising administering to the mammal a composition comprising a zvegf3 antagonist in combination with a pharmaceutically acceptable delivery vehicle, wherein the zvegf3 antagonist is selected from the group consisting of anti-zvegf3 antibodies, mitogenically inactive receptor-binding zvegf3 variant polypeptides, and inhibitory polynucleotides, in an amount sufficient to reduce cell proliferation or extracellular matrix production. Within certain embodiments of the invention, proliferation of mesangial, endothelial, smooth muscle, fibroblast, osteoblast, osteoclast, stellate, or interstitial cells is reduced. Within other embodiments, the mammal is suffering from a fibroproliferative disorder of the liver, kidney, or bone.

Within another aspect of the present invention there is provided a method of treating fibrosis in a mammal comprising administering to the mammal a composition comprising a therapeutically effective amount of a zvegf3 antagonist in combination with a pharmaceutically acceptable delivery vehicle, wherein the zvegf3 antagonist is selected from the group consisting of anti-zvegf3 antibodies, mitogenically inactive receptor-binding zvegf3 variant polypeptides, and inhibitory polynucleotides. Within certain embodiment of the invention the fibrosis is liver fibrosis or kidney fibrosis.

Within a third aspect of the invention there is provided a method of reducing stellate cell activation in a mammal comprising administering to the mammal a composition comprising a zvegf3 antagonist in combination with a pharmaceutically acceptable delivery vehicle, wherein the zvegf3 antagonist is selected from the group consisting of anti-zvegf3 antibodies, mitogenically inactive receptor-binding zvegf3 variant polypeptides, and inhibitory polynucleotides, in an amount sufficient to reduce stellate cell activation. Within one embodiment, the stellate cells are liver stellate cells.

Within a fourth aspect of the invention there are provided pharmaceutical compositions for use within the above methods. In general, the compositions comprise a zvegf3 antagonist in combination with a pharmaceutically acceptable delivery vehicle, wherein the zvegf3 antagonist is selected from the group consisting of anti-zvegf3 antibodies, mitogenically inactive receptor-binding zvegf3 variant polypeptides, and inhibitory polynucleotides.

Figure 1G:
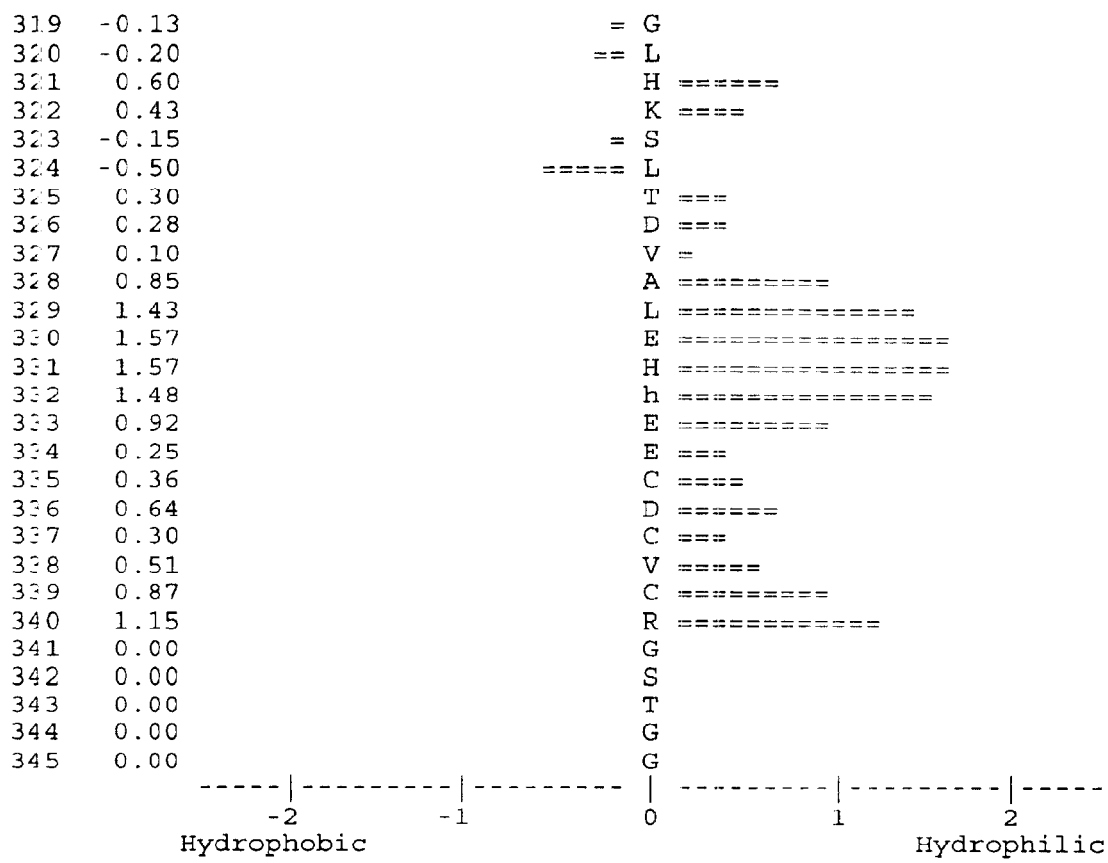

These and other aspects of the invention will become evident upon reference to the following detailed description of the invention and the attached drawings. In the drawings:

Figure 1B:
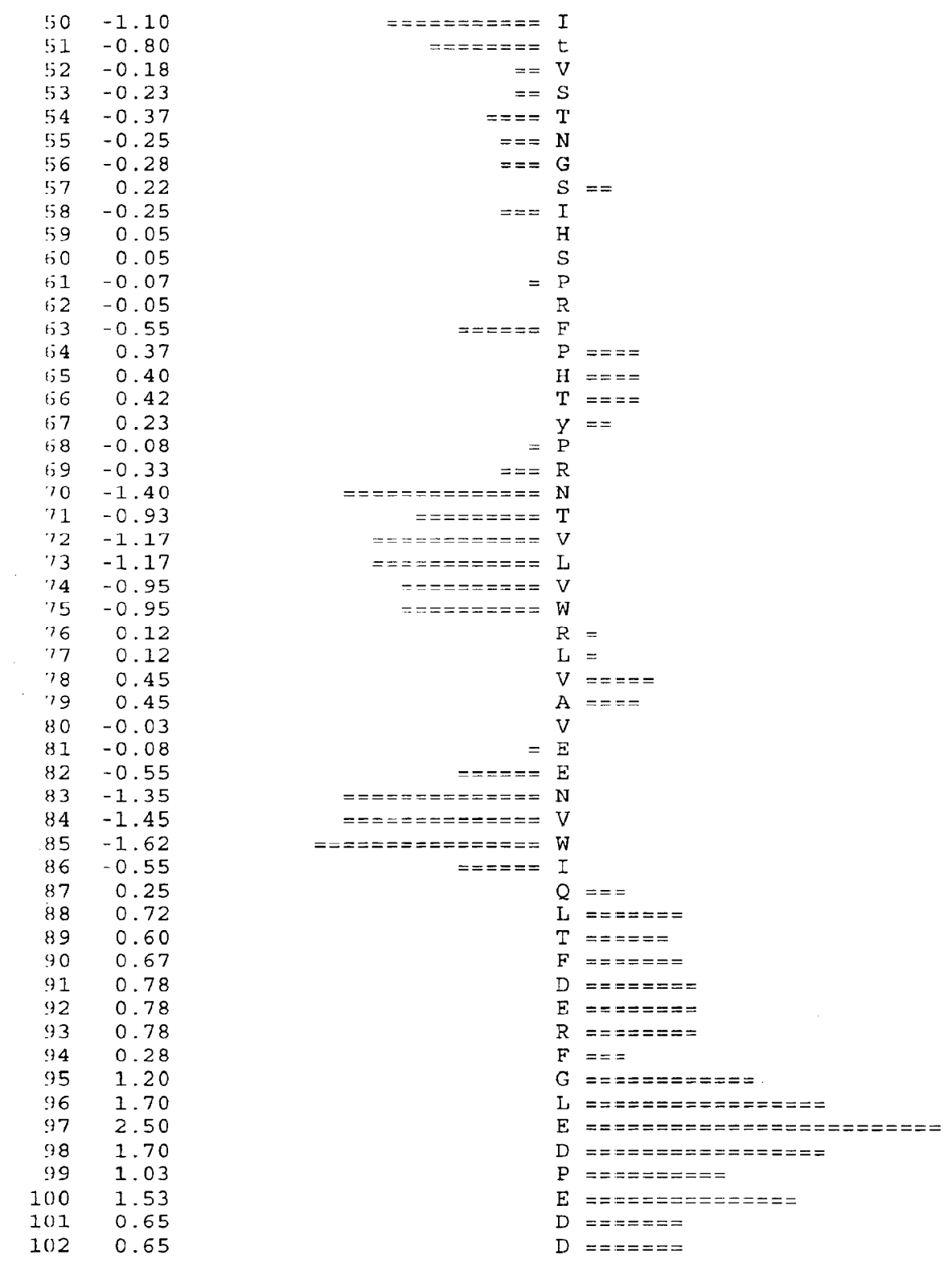
Figure 1C:
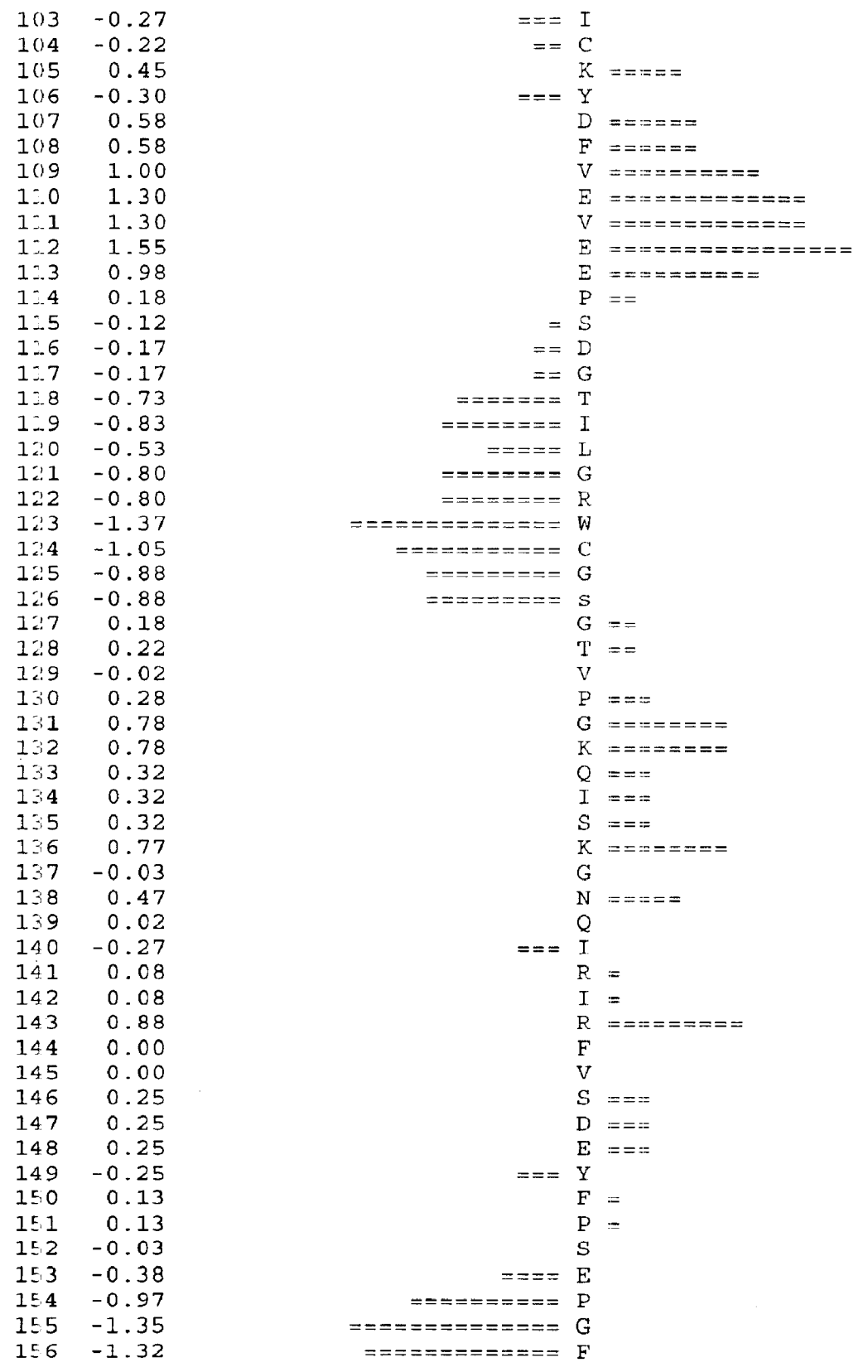
Figure 1D:
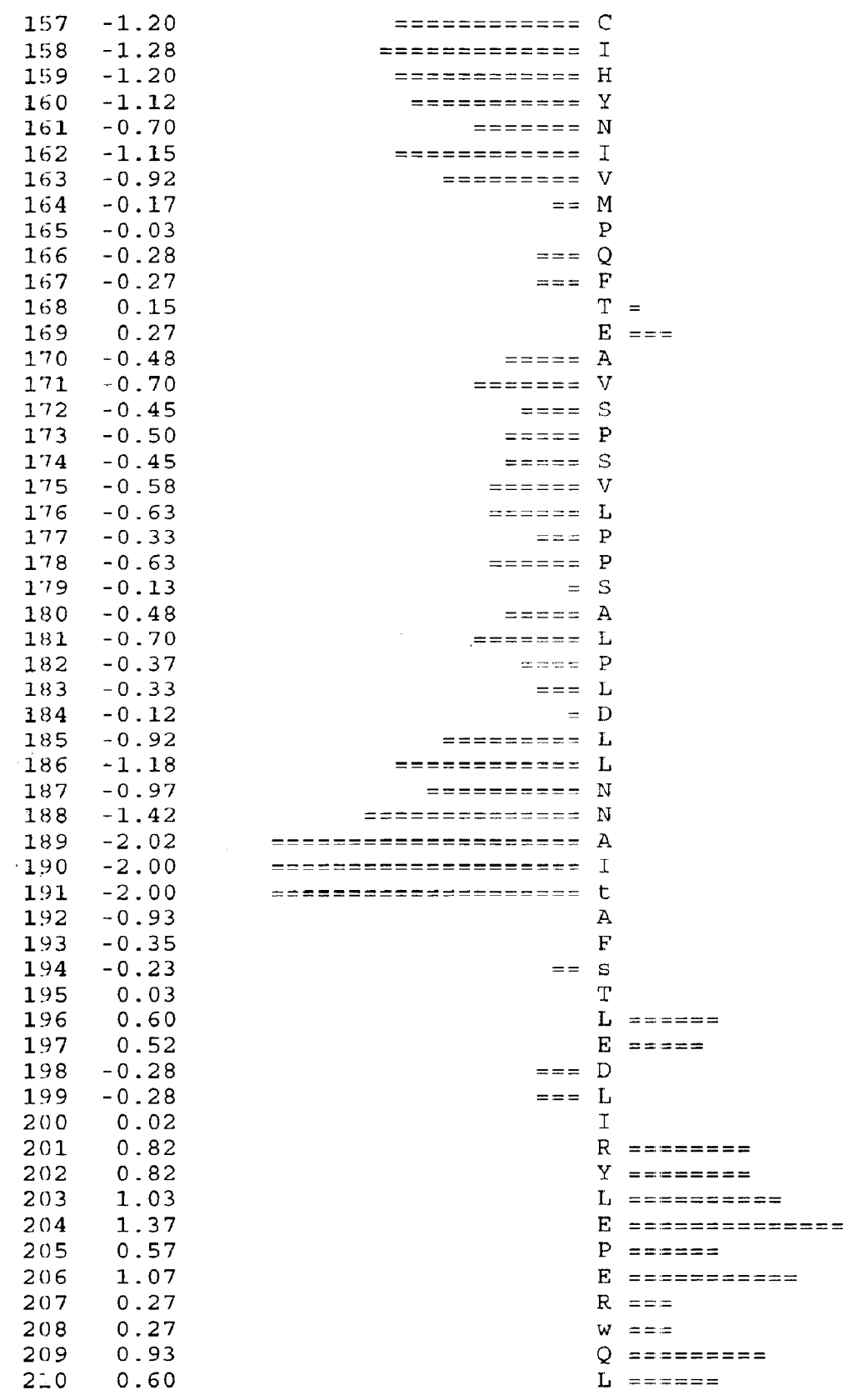
Figure 1E:
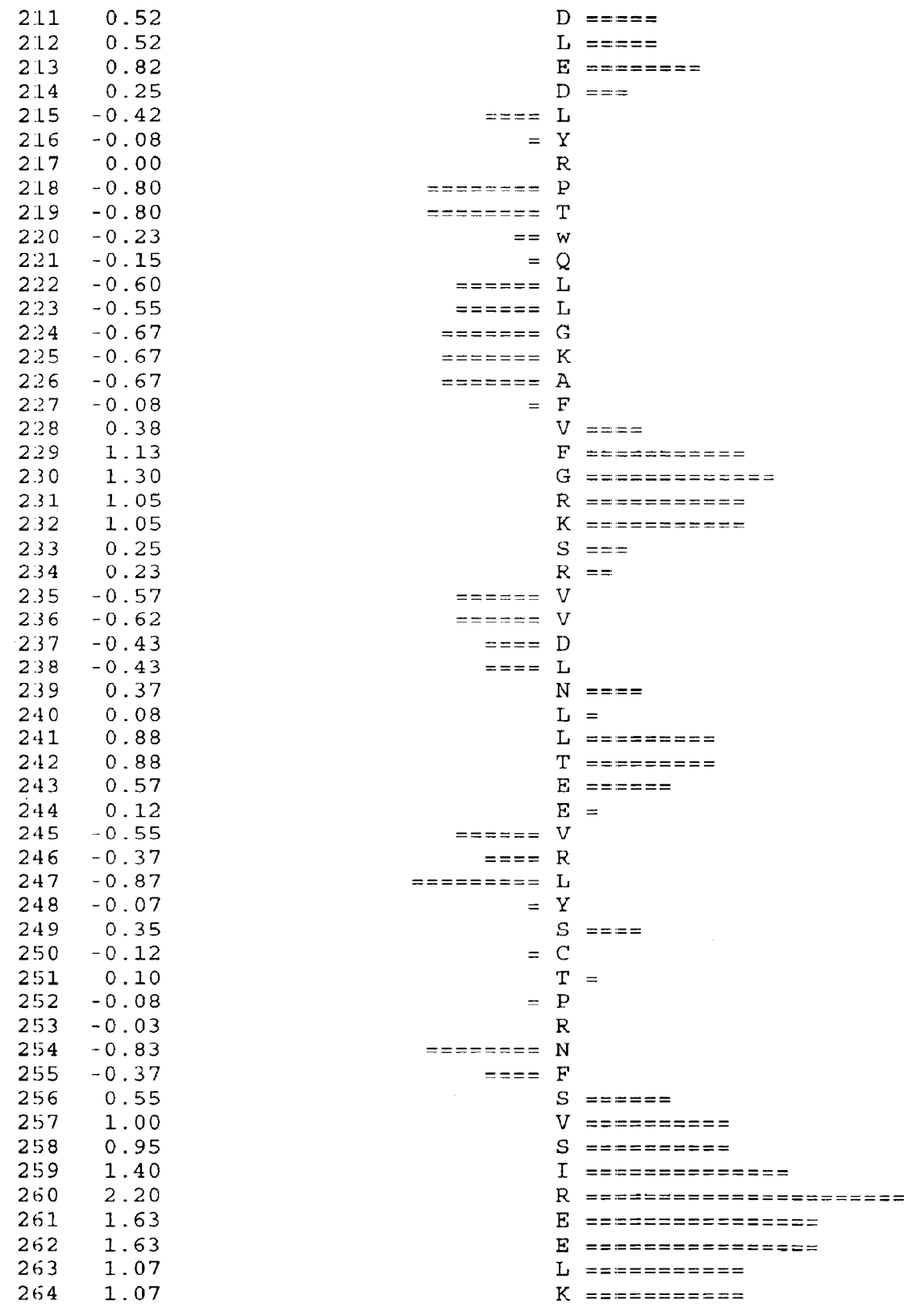

FIGS. 1A–1G are a Hopp/Woods hydrophilicity profile of the amino acid sequence shown in SEQ ID NO:2. The profile is based on a sliding six-residue window. Buried G, S, and T residues and exposed H, Y, and W residues were ignored. These residues are indicated in the figure by lower case letters.

FIG. 2 is an alignment of human (SEQ ID NO-2) and mouse (SEQ ID NO:4) amino acid sequences.

The term "antagonist" is used herein to denote a compound that reduces a biological activity of another compound. Within the present invention, a "zvegf3 antagonist" is a compound that reduces the receptor-mediated biological activity (e.g., mitogenic activity) of zvegf3 on a target cell. Antagonists may exert their action by competing with zvegf3 for binding sites on a cell-surface receptor, by binding to zvegf3 and preventing it from binding to a cell-surface receptor, by otherwise interfering with receptor function, by reducing production of zvegf3, or by other means.

"Extracellular matrix" (ECM) is a complex mixture of macromolecules that accumulates within tissues in close apposition to cell surfaces. ECM contains secreted macromolecules such as collagens I, m and IV, fibronectin, laminins, and various proteoglycans. These macromolecules can be organized to provide cohesion to the tissue and can contribute to its structural and mechanical properties. ECM can act as a depository for, and release site of, potent secreted growth factors, and is known to influence growth, survival and differentiation of the cells it surrounds. Pathologic ECM accumulation, if unchecked, can restrict access of nutrients, growth factors and other physiologically important molecules to cells and can lead to the creation of areas of low live cell density. Over time, this accumulation can result in the inability of a tissue to perform its specific metabolic and structural roles, and may ultimately lead to overt cell and tissue death.

An "inhibitory polynucleotide" is a DNA or RNA molecule that reduces or prevents expression (transcription or translation) of a second (target) polynucleotide. Inhibitory polynucleotides include antisense polynucleotides, ribozymes, and external guide sequences. The term "inhibitory polynucleotide" further includes DNA and RNA molecules that encode the actual inhibitory species, such as DNA molecules that encode ribozymes.

The terms "treat" and "treatment" are used broadly to denote therapeutic and prophylactic interventions that favorably alter a pathological state. Treatments include procedures that moderate or reverse the progression of, reduce the severity of, prevent, or cure a disease.

All references cited herein are incorporated by reference in their entirety.

The present invention provides methods for treating fibrosis in a patient using zvegf3 antagonists. Zvegf3 is a protein that is structurally related to platelet-derived growth factor (PDGF) and the vascular endothelial growth factors (VEGF). This protein has also been designated "VEGF-R" (WIPO Publication WO 99/37671) and, more recently, "PDGF-C" (WO 00/18212). Zvegf3/PDGF-C is a multi-domain protein with significant homology to the PDGF/VEGF family of growth factors. Representative amino acid sequences of human and mouse zvegf3 are shown in SEQ ID NO:2 and SEQ ID NO:4, respectively. DNAs encoding these polypeptides are shown in SEQ ID NOS:1 and 3, respectively.

The term "zvegf3 protein" is used herein to denote proteins comprising the growth factor domain of a zvegf3 polypeptide (e.g., residues 235–345 of human zvegf3 (SEQ ID NO:2) or mouse zvegf3 (SEQ ID NO:4)), wherein said protein is mitogenic for cells expressing cell-surface PDGF α-receptor subunit Zvegf3 has been found to bind to the αα and αβ isoforms of PDGF receptor. Zvegf3 proteins include homodimers and heterodimers as disclosed below. Using methods known in the art, zvegf3 proteins can be prepared in a variety of forms, including glycosylated or non-glycosylated, pegylated or non-pegylated, with or without an initial methionine residues, and as fusion proteins as disclosed in more detail below.

Structural predictions based on the zvegf3 sequence and its homology to other growth factors suggests that the polypeptide can form homomultimers or heteromultimers having growth factor activity, i.e., modulating one or more of cell proliferation, migration, differentiation, and metabolism. Experimental evidence confirms that biologically active zvegf3 is a dimeric protein. While not wishing to be bound by theory, the similarity of zvegf3 to other members of the PDGF/VEGF family suggests that zvegf3 may also form heteromultimers with other members of the family, including VEGF, VEGF-B, VEGF-C, VEGF-D, zvegf4 (SEQ ID NO:5), PlGF (Maglione et al., *Proc. Natl. Acad. Sci. USA* 88:9267–9271, 1991), PDGF-A (Murray et al., U.S. Pat. No. 4,899,919; Heldin et al., U.S. Pat. No. 5,219, 759), or PDGF-B (Chiu et al., *Cell* 37:123–129, 1984; Johnsson et al., *EMBO J.* 3:921–928, 1984).

The zvegf3 polypeptide chain comprises a growth factor domain and a CUB domain. The growth factor domain is characterized by an arrangement of cysteine residues and beta strands that is characteristic of the "cystine knot" structure of the PDGF family. The CUB domain shows sequence homology to CUB domains in the neuropilins (Takagi et al., *Neuron* 7:295–307, 1991; Soker et al., ibid.), human bone morphogenetic protein-i (Wozney et al., *Science* 242:1528–1534, 1988), porcine seminal plasma protein and bovine acidic seminal fluid protein (Romero et al., *Nat. Struct. Biol.* 4:783–788, 1997), and *X. laevis* tolloid-like protein (Lin et al., *Dev. Growth Differ.* 39:43–51, 1997).

An alignment of mouse and human zvegf3 polypeptide sequences is shown in FIG. 2. Analysis of the amino acid sequence shown in SEQ ID NO:2 indicates that residues 1 to 14 form a secretory peptide. The CUB domain extends from residue 46 to residue 163. A propeptide-like sequence extends from residue 164 to residue 234, and includes two potential cleavage sites at its carboxyl terminus, a dibasic site at residues 231–232 and a target site for furin or a furin-like protease at residues 231–234. The growth factor domain extends from residue 235 to residue 345. Those skilled in the art will recognize that domain boundaries are somewhat imprecise and can be expected to vary by up to +5 residues from the specified positions. Potential proteolytic cleavage sites occur at residues 232 and 234. Processing of recombinant zvegf3 produced in BHK cells has been found to occur between residues 225 and 226. Signal peptide cleavage is predicted to occur after residue 14 (±3 residues). This analysis suggests that the zvegf3 polypeptide chain may be cleaved to produce a plurality of monomeric species as shown in Table 1. Cleavage after Arg-234 is expected to result in subsequent removal of residues 231–234, with possible conversion of Gly-230 to an amide. Cleavage after Lys-232 is expected to result in subsequent removal of residue 231, again with possible conversion of Gly-230 to an amide. In addition, it may be advantageous to include up to seven residues of the interdomain region at the carboxyl terminus of the CUB domain. The interdomain region can be truncated at its amino terminus by a like amount. See Table 1. Corresponding domains in mouse and other non-human zvegf3s can be determined by those of ordinary skill in the art from sequence alignments.

TABLE 1

| Monomer | Residues (SEQ ID NO:2) |
| --- | --- |
| Cub domain | 15–163 |
|  | 46–163 |
|  | 15–170 |
|  | 46–170 |
| CUB domain + interdomain region | 15–234 |
|  | 46–234 |
|  | 15–229 amide |
|  | 15–230 |
| Cub domain + interdomain region + growth factor domain | 15–345 |
|  | 46–345 |
| Growth factor domain | 235–345 |
|  | 226–345 |
| Growth factor domain + interdomain region | 164–345 |
|  | 171–345 |

Zvegf3 can thus be prepared in a variety of multimeric forms comprising a zvegf3 polypeptide as disclosed above. These zvegf3 polypeptides include zvegf3$_{15-345}$, zvegf$_{46-345}$, zvegf3$_{226-345}$, and zvegf3$_{235-345}$. Variants and derivatives of these polypeptides can also be prepared as disclosed herein.

Zvegf3 proteins can be prepared as fusion proteins comprising amino- or carboxyl-terminal extensions, such as an amino-terminal methionine residue, an affinity tag, or a targetting polypeptide. For example, a zvegf3 protein can be prepared as a fusion with an affinity tag to facilitate purification. In principal, any peptide or protein for which an antibody or other specific binding agent is available can be used as an affinity tag. Affinity tags include, for example, a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu—Glu affinity tag (Grussenmeyer et al., *Proc. Natl. Acad. Sci. USA* 82:7952–4, 1985), substance P, Flag™ peptide (Hopp et al., *Biotechnology* 6:1204–1210, 1988), streptavidin binding peptide, maltose binding protein (Guan et al., *Gene* 67:21–30, 1987), cellulose binding protein, thioredoxin, ubiquitin, T7 polymerase, or other antigenic epitope or binding domain. Fusion of zvegf3 to, for example, maltose binding protein or glutatione S transferase can be used to improve yield in bacterial expression systems. In these instances the non-zvegf3 portion of the fusion protein ordinarily will be removed prior to use. Separation of the zvegf3 and non-zvegf3 portions of the fusion protein is facilitated by providing a specific cleavage site between the two portions. Such methods are well known in the art. Zvegf3 can also be fused to a targetting peptide, such as an antibody (including polyclonal antibodies, monoclonal antibodies, antigen-binding fragments thereof such as $F(ab')_2$ and Fab fragments, single chain antibodies, and the like) or other peptidic moiety that binds to a target tissue.

Variations can be made in the zvegf3 amino acid sequences shown in SEQ ID NO:2 and SEQ ID NO:4 to provide mitogenically inactive, receptor-binding polypeptides that act as zvegf3 antagonists. As used herein, the term "mitogenically inactive" means that the protein does not show statistically significant activity in a standard mitogenesis assay as compared to a wild-type zvegf3 control. Such variations include amino acid substitutions, deletions, and insertions. While not wishing to be bound by theory, it is believed that residues Arg260–Trp271 of human zvegf3 (SEQ ID NO:2) form a loop that define the ability of the protein to bind to PDGF-β receptors, although binding is also permitted to alpha receptors. It is thus predicted that binding to either receptor subunit can be blocked or enhanced by mutations in this region. In addition, residues Leu311–His321 of SEQ ID NO:2 are predicted to form a loop (loop3) that may be mutated to block receptor binding. Peptides that mimic this region of the molecule may act as antagonists.

The effects of amino acid sequence changes can be predicted by computer modeling (using, e.g., the Insight II® viewer and homology modeling tools; MSI, San Diego, Calif.) or determined by analysis of crystal structure (see, e.g., Lapthorn et al., *Nature* 369:455, 1994), and can be assessed using art-recognized mutagenesis procedures in combination with activity assays. Representative mutagenesis procedures include, for example, site-directed mutagenesis and alanine-scanning mutagenesis (Cunningham and Wells, *Science* 244, 1081–1085, 1989; Bass et al., *Proc. Natl. Acad. Sci. USA* 88:44984502, 1991). Multiple amino acid substitutions can be made and tested using known methods, such as those disclosed by Reidhaar-Olson and Sauer (*Science* 241:53–57, 1988) or Bowie and Sauer (*Proc. Natl Acad Sci. USA* 86:2152–2156, 1989). Other methods that can be used include phage display (e.g., Lowman et al., *Biochem* 30:10832–10837, 1991; Ladner et al., U.S. Pat. No. 5,223,409; Huse, WIPO Publication WO 92/06204), region-directed mutagenesis (Derbyshire et al., *Gene* 46:145, 1986; Ner et al., DNA 7:127, 1988), and DNA shuffling as disclosed by Stemmer (*Nature* 370:389–391, 1994) and Stemmer (*Proc. Natl. Acad. Sci. USA* 91:10747–10751, 1994). The resultant mutant molecules are tested for mitogenic activity or other properties (e.g., receptor binding) to identify amino acid residues that are critical to these functions. Mutagenesis can be combined with high volume or high-throughput screening methods to detect biological activity of zvegf3 variant polypeptides, in particular biological activity in modulating cell proliferation. For example, mitogenesis assays that measure dye incorporation or $^3$H-thymidine incorporation can be carried out on large numbers of samples. Competition assays can be employed to confirm antagonist activity.

Zvegf3 proteins, including full-length polypeptides, fragments, and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms). Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., eds., *Current Protocols in Molecular Biology, Green and Wiley and Sons, NY,* 1993. See, WO 00/34474. In general, a DNA sequence encoding a zvegf3 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers. See, WO 00/34474.

Zvegf3 proteins can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al.,

*Proc. Natl. Acad. Sci. USA* 90:10145–10149, 1993). In a second method, translation is carried out in *Xenopus* oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

Zvegf3 polypeptides or fragments thereof can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989.

Zvegf3 proteins are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321–1325, 1988. Furthermore, the growth factor domain itself binds to nickel resin at pH 7.0–8.0 and 25 mM Na phosphate, 0.25 M NaCl. Bound protein can be eluted with a descending pH gradient down to pH 5.0 or an imidazole gradient. Recombinant zvegf3 growth factor domain protein can be purified using a combination of chromatography on a strong cation exchanger followed by a tandem column array comprising a strong anion exchanger followed by an immobilized metal affinity column in series. It has also been found that zvegf3 binds to various dye matrices (e.g., BLUE1, BLUE 2, ORANGE 1, ORANGE 3, and RED3 from Lexton Scientific, Signal Hill, Calif.) in PBS at pH 6–8, from which the bound protein can be eluted in 1–2 M NaCl in 20 mM boric acid buffer at pH 8.8. Protein eluted from RED3 may be passed over RED2 (Lexton Scientific) to remove remaining contaminants. Proteins comprising a glu—glu tag can be purified by immunoaffinity chromatography according to conventional procedures. See, for example, Grussenmeyer et al., *ibid*. Maltose binding protein fusions are purified on an amylose column according to methods known in the art.

As disclosed in more detail below, overexpression of zvegf3 in the livers of transgenic mice led to marked stellate cell activation and proliferation. At 8 weeks of age there was an accumulation of perisinusiodal extracellular matrix (ECM) that progressed to a perivenular ECM deposition at 22 weeks and possible eary stages of cirrhosis characterized by fibrotic banding and hepatic nodule formation at 33 weeks of age. Thus, zvegf3 dimers appear to resemble the previously described PDGF isoforms in being potent mitogens of hepatic stellate cells and appearing to play a role in liver fibrosis. These transgenic mice thus provide a model for testing zvegf3 antagonists as well as other antifibrotic agents. In view of these and other experiments disclosed herein, it is expected that altered zvegf3 expression may initiate or exacerbate a variety of fibrotic conditions. In this context, inhibiting the action of zvegf3 using a zvegf3 antagonist will limit the progress of such conditions. While not wishing to be bound by theory, it is believed that the pro-fibrotic effects of zvegf3 are due at least in part to the induction of TGF-β production.

Zvegf3 antagonists include, without limitation, anti-zvegf3 antibodies (including neutralizing antibodies), inhibitory polynucleotides (including antisense polynucleotides, ribozymes, and external guide sequences), and other peptidic and non-peptidic agents, including small molecule inhibitors and mitogenically inactive receptor-binding zvegf3 polypeptides. Such antagonists can be use to block the mitogenic effects of zvegf3 and thereby reduce, inhibit, prevent, or otherwise treat fibrosis, including, without limitation, scar formation, keloids, scleroderma, liver fibrosis, lung fibrosis, kidney fibrosis, pancreatic fibrosis, myelofibrosis, post-surgical fibrotic adhesions, fibroproliferative disorders of the vasculature, fibroproliferative disorders of the prostate, fibroproliferative disorders of bone, fibromatosis, fibroma, fibrosarcoma, and the like.

Of particular interest is the use of zvegf3 or zvegf3 antagonists for the treatment or repair of liver damage, including damage due to chronic liver disease, including chronic active hepatitis (including hepatitis C) and many other types of cirrhosis. Widespread, massive necrosis, including destruction of virtually the entire liver, can be caused by, *inter alia*, fulminant viral hepatitis; overdoses of the analgesic acetaminophen; exposure to other drugs and chemicals such as halothane, monoamine oxidase inhibitors, agents employed in the treatment of tuberculosis, phosphorus, carbon tetrachloride, and other industrial chemicals. Conditions associated with ultrastructural lesions that do not necessarily produce obvious liver cell necrosis include Reye's syndrome in children, tetracycline toxicity, and acute fatty liver of pregnancy. Cirrhosis, a diffuse process characterized by fibrosis and a conversion of normal architecture into structurally abnormal nodules, can come about for a variety reasons including alcohol abuse, post necrotic cirrhosis (usually due to chronic active hepatitis), biliary cirrhosis, pigment cirrhosis, cryptogenic cirrhosis, Wilson's disease, and alpha-1-antitrypsin deficiency. In cases of liver fibrosis it may be beneficial to administer a zvegf3 antagonist to suppress the activation of stellate cells, which have been implicated in the production of extracellular matrix in fibrotic liver (Li and Friedman, *ibid.*).

Fibrotic disorders of the kidney include, without limitation, glomerulonephritis (including membranoproliferative, diffuse proliferative, rapidly progressive, and chronic forms), diabetic glomerulosclerosis, focal glomerulosclerosis, diabetic nephropathy, lupus nephritis, tubulointerstitial fibrosis, membranous nephropathy, amyloidosis (which affects the kidney among other tissues), renal arteriosclerosis, and nephrotic syndrome. The glomerulus is a major target of many types of renal injury, including immunologic (e.g., immune-complex- or T-cell-mediated), hemodynamic (systemic or renal hypertension), metabolic (e.g., diabetes), "atherosclerotic" (accumulation of lipids in the glomerulus), infiltrative (e.g., amyloid), and toxic (e.g., snake venom) (Johnson, *Kidney Int.* 45:1769–1782, 1994). The renal structural changes in patients with diabetic nephropathy include hypertrophy of the glomerulus, thickening of the glomerular and tubular membranes (due to accumulated matrix), and increased amounts of matrix in the measangium and tubulointerstitium (Ziyadeh et al., *Proc. Natl. Acad. Sci. USA* 97:8015–8020, 2000). Glomerular hypertension due to intrarenal hemodynamic changes in diabetes can contribute to the progression of diabetic nephropathy (Ishida et al., *Diabetes* 48:595–602, 1999). Autoimmune nephritis can also lead to altered mesangial cell growth responses (Liu and Ooi, *J. Immunol.* 151:2247–2251, 1993). Infection by hepatitis-C virus can also result in idiopathic membranoproliferative glomerulonephritis (Johnson et al., *N. Engl. J. Med.* 328:465470, 1993). While not wishing to be bound by theory, experiments have shown that the activity of zvegf3 is mediated by the $\alpha\alpha$ and $\alpha\beta$ PDGF receptor isoforms. PDGF receptors are widely expressed in most renal cell types, and their expression is upregulated in a number of kidney pathologies (e.g., Iida et al., *Proc. Natl. Acad. Sci. USA* 88:6560–6564, 1991). Stimulation of PDGF receptors has been implicated in fibroproliferative diseases of the kidney in a variety of animal models (e.g., Ooi et al., *P.S.E.B.M.* 213:230–237, 1996; Lindahl et al., *Development* 125:3313–3322, 1998; Lindahl and Betsholtz, *Curr. Op. Nephr. Hypert.* 7:21–26, 1998; and Betsholtz and Raines, *Kidney Int.* 51:1361–1369, 1997).

Fibrotic disorders of the lung include, for example, silicosis, asbestosis, idiopathic pulmonary fibrosis, bronchiolitis obliterans-organizing pneumonia, pulmonary fibrosis associated with high-dose chemotherapy, idiopathic pulmonary fibrosis, and pulmonary hypertension. These diseases are characterized by cell proliferation and increased production of extracellular matrix components, such as collagens, elastin, fibronectin, and tenascin-C.

Pancreatic fibrosis occurs in chronic pancreatitis. This condition is characterized by duct calcification and fibrosis of the pancreatic parenchyma. Like liver cirrhosis, chronic pancreatitis is associated with alcohol abuse. See, Fogar et al., *J. Medicine* 29:277–287, 1998.

Diseases of the skeleton that are due to modified growth and matrix production in the bone include, but are not limited to, osteopetrosis, hyperostosis, osteosclerosis, osteoarthritis, and endosteal bone formation in metastatic prostate cancer. Fibroproliferative disorders of bone are characterized by aberrant and ectopic bone formation, commonly seen as active proliferation of the major cell types participating in bone formation as well as elaboration by those cells of a complex bone matrix. Exemplary of such bone disorders is the fibrosis that occurs with prostate tumor metastases to the axial skeleton. In prostate tumor-related cancellous bone growth, prostate carcinoma cells can interact reciprocally with osteoblasts to produce enhanced tumor growth and osteoblastic action when they are deposited in bone (Zhau et al., *Cancer* 88:2995–3001, 2000; Ritchie et al., *Endocrinology* 138:1145–1150, 1997). Fibroproliferative responses of the bone originating in the skeleton per se include ostepetrosis and hyperstosis. A defect in osteoblast differentiation and function is thought to be a major cause in osteopetrosis, an inherited disorder characterized by bone sclerosis due to reduced bone resorption, marrow cavities fail to develop, resulting in extramedullary hematopoiesis and severe hematologic abnormalities associated with optic atrophy, deafness, and mental retardation (Lajeunesse et al., *J. Clin Invest.* 98:1835–1842, 1996). In osteoarthritis, bone changes are known to occur, and bone collagen metabolism is increased within osteoarthritic femoral heads. The greatest changes occur within the subchondral zone, supporting a greater proportion of osteoid in the diseased tissue (Mansell and Bailey, *J. Clin. Invest.* 101:1596–1603, 1998). As shown in more detail below, zvegf3 has been found to be produced by prostate cells and to stimulate an osteoblast cell line.

Fibroproliferative disorders of the vasculature include, for example, transplant vasculopathy, which is a major cause of chronic rejection of heart transplantation. Transplant vasculopathy is characterized by accelerated atherosclerotic plaque formation with diffuse occlusion of the coronary arteries, which is a "classic" fibroproliferative disease. See, Miller et al., *Circulation* 101:1598–1605, 2000).

Antibodies used as zvegf3 antagonists include antibodies that specifically bind to a zvegf3 protein and, by so binding, reduce or prevent the binding of zvegf3 protein to the receptor and, consequently, reduce or block the receptor-mediated activity of zvegf3. As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Monoclonal antibodies can also be produced in mice that have been genetically altered to produce antibodies that have a human structure.

Methods for preparing and isolating polyclonal and monoclonal antibodies are well known in the art. See, for example, Cooligan et al. (eds.), *Current Protocols in Immunology*, National Institutes of Health, John Wiley and Sons, Inc., 1995; Sambrook et al., *Molecular Cloning: A Laboratory Manual*, second edition, Cold Spring Harbor, N.Y., 1989; and Hurrell (ed.), *Monoclonal Hybridoma Antibodies: Techniques and Applications*, CRC Press, Inc., Boca Raton, Fla., 1982. As would be evident to one of ordinary skill in the art, polyclonal antibodies can be generated by inoculating a variety of warm-blooded animals such as horses, cows, goats, sheep, dogs, chickens, rabbits, mice, and rats with a zvegf3 polypeptide or a fragment thereof.

Immunogenic polypeptides will comprise an epitope-bearing portion of a zvegf3 polypeptide (e.g., as shown in SEQ ID NO:2) or receptor. An "epitope" is a region of a protein to which an antibody can bind. See, for example, Geysen et at., *Proc. Natl. Acad. Sci. USA* 81:39984002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660–666, 1983. Immunogenic, epitope-bearing polypeptides contain a sequence of at least six, often at least nine, more often from 15 to about 30 contiguous amino acid residues of a zvegf3 protein. Polypeptides comprising a larger portion of a zvegf3 protein, i.e. from 30 to 50 residues up to the entire sequence are included. It is preferred that the amino acid sequence of the epitope-bearing polypeptide is selected to provide substantial solubility in aqueous solvents, that is the sequence includes relatively hydrophilic residues, and hydrophobic residues are substantially avoided. Such regions include residues 43–48, 96–101, 97–102, 260–265, and 330–335 of SEQ ID NO:2. As noted above, it is generally preferred to use somewhat longer peptides as immunogens, such as a peptide comprising residues 80–104, 299–314, and 299–326 of SEQ ID NO:2. The latter peptide can be prepared with an additional N-terminal Cys residue to facilitate coupling.

The immunogenicity of a polypeptide immunogen may be increased through the use of an adjuvant, such as alum (aluminum hydroxide) or Freund's complete or incomplete adjuvant. Polypeptides useful for immunization also include fusion polypeptides, such as fusions of a zvegf3 polypeptide or a portion thereof with an immunoglobulin polypeptide or with maltose binding protein. If the polypeptide portion is "hapten-like", such portion may be advantageously joined or linked to a macromolecular carrier (such as keyhole limpet hemocyanin (KLH), bovine serum albumin (BSA), or tetanus toxoid) for immunization.

Alternative techniques for generating or selecting antibodies include in vitro exposure of lymphocytes to a polypeptide immunogen, and selection of antibody display libraries in phage or similar vectors (for instance, through use of immobilized or labeled polypeptide). Techniques for creating and screening such random peptide display libraries are known in the art (e.g., Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698), and random peptide display libraries and kits for screening such libraries are available commercially, for instance from Clontech Laboratories (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the zvegf3 sequences disclosed herein to identify proteins which bind to zvegf3.

Antibodies are determined to be specifically binding if they bind to their intended target (e.g., zvegf3 protein or receptor) with an affinity at least 10-fold greater than the binding affinity to control (e.g., non-zvegf3 or non-receptor) polypeptide or protein. In this regard, a "non-zvegf3 polypeptide" includes the related molecules VEGF, VEGF-B, VEGF-C, VEGF-D, PlGF, PDGF-A, and PDGF-B, but excludes zvegf3 polypeptides from non-human species. Due to the high level of amino acid sequence identity expected between zvegf3 orthologs, antibodies specific for human zvegf3 may also bind to zvegf3 from other species. The binding affinity of an antibody can be readily determined by one of ordinary skill in the art, for example, by Scatchard analysis (Scatchard, G., Ann. NY Acad. Sci. 51: 660–672, 1949). Methods for screening and isolating specific antibodies are well known in the art. See, for example, Paul (ed.), Fundamental Immunology, Raven Press, 1993; Getzoff et al., Adv. in Immunol. 43:1–98, 1988; Goding (ed.), Monoclonal Antibodies: Principles and Practice, Academic Press Ltd., 1996; Benjamin et al., Ann. Rev. Immunol. 2:67–101, 1984.

Binding affinity can also be determined using a commercially available biosensor instrument (BIAcore™, Pharmacia Biosensor, Piscataway, N.J.), wherein protein is immobilized onto the surface of a receptor chip. See, Karlsson, J. Immunol. Methods 145:229–240, 1991 and Cunningham and Wells, J. Mol. Biol. 234:554–563, 1993. This system allows the determination of on- and off-rates, from which binding affinity can be calculated, and assessment of stoichiometry of binding.

A variety of assays known to those skilled in the art can be utilized to detect antibodies that specifically bind to zvegf3 proteins or receptors. Exemplary assays are described in detail in Antibodies: A Laboratory Manual, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assays, inhibition or competition assays, and sandwich assays.

For therapeutic applications it is generally preferred to use neutralizing antibodies. As used herein, the term "neutralizing antibody" denotes an antibody that inhibits at least 50% of the biological activity of the cognate antigen when the antibody is added at a 1000-fold molar access. Those of skill in the art will recognize that greater neutralizing activity is sometimes desirable, and antibodies that provide 50% inhibition at a 100-fold or 10-fold molar access may be advantageously employed.

Zvegf3 antagonists further include antisense polynucleotides, which can be used to inhibit zvegf3 gene transcription and thereby inhibit cell activation and/or proliferation in vivo. Polynucleotides that are complementary to a segment of a zvegf3-encoding polynucleotide (e.g., a polynucleotide as set forth in SEQ ID NO:1) are designed to bind to zvegf3-encoding mRNA and to inhibit translation of such mRNA. Antisense polynucleotides can be targetted to specific tissues using a gene therapy approach with specific vectors and/or promoters, such as viral delivery systems as disclosed in more detail below.

Ribozymes can also be used as zvegf3 antagonists within the present invention. Ribozymes are RNA molecules that contain a catalytic center and a target RNA binding portion. The term includes RNA enzymes, self-splicing RNAs, self-cleaving RNAs, and nucleic acid molecules that perform these catalytic functions. A ribozyme selectively binds to a target RNA molecule through complementary base pairing, bringing the catalytic center into close proximity with the target sequence. The ribozyme then cleaves the target RNA and is released, after which it is able to bind and cleave additional molecules. A nucleic acid molecule that encodes a ribozyme is termed a "ribozyme gene." Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). An expression vector can be constructed in which a regulatory element is operably linked to a nucleotide sequence that encodes a ribozyme.

In another approach, expression vectors can be constructed in which a regulatory element directs the production of RNA transcripts capable of promoting RNase P-mediated cleavage of mRNA molecules that encode a zvegf3 polypeptide. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053; Yuan et al., Science 263:1269, 1994; Pace et al., WIPO Publication No. WO 96/18733; George et al., WIPO Publication No. WO 96/21731; and Werner et al., WIPO Publication No. WO 97/33991). An external guide sequence generally comprises a ten- to fifteen-nucleotide sequence complementary to zvegf3 mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

The growth factor domain of zvegf3 has been found to be the active (PDGF receptor-binding) species of the molecule. Proteolytic processing to remove the N-terminal portion of the molecule is required for activation. Thus, inhibitors of this proteolytic activation can also be used as zvegf3 antagonists within the present invention.

For pharmaceutical use, zvegf3 antagonists are formulated for topical or parenteral, particularly intravenous or subcutaneous, delivery according to conventional methods. In general, pharmaceutical formulations will include a zvegf3 antagonist in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in *Remington: The Science and Practice of Pharmacy*, Gonda, ed., Mack Publishing Co., Easton, Pa., 19th ed., 1995. A "therapeutically effective amount" of a composition is that amount that produces a statistically significant effect, such as a statistically significant reduction in disease progression or a statistically significant improvement in organ function. The exact dose will be determined by the clinician according to accepted standards, taking into account the nature and severity of the condition to be treated, patient traits, etc. Determination of dose is within the level of ordinary skill in the art. The therapeutic formulations will generally be administered over the period required to achieve a beneficial effect, commonly up to several months and, in treatment of chronic conditions, for a year or more. Dosing is daily or intermittently over the period of treatment. Intravenous administration will be by bolus injection or infusion over a typical period of one to several hours. Sustained release formulations can also be employed. For treatment of pulmonary fibrosis, a zvegf3 antagonist can be delivered by aerosolization according to methods known in the art. See, for example, Wang et al., U.S. Pat. No. 5,011,678; Gonda et al., U.S. Pat. No. 5,743,250, and Lloyd et al., U.S. Pat. No. 5,960,792.

Other mitogenic factors, including EGF, TGFβ, and FGF, have been implicated in the initiation or perpetuation of fibrosis. It may therefore be advantageous to combine a zvegf3 inhibitor with one or more inhibitors of these other factors.

Antibodies are preferably administered parenterally, such as by bolus injection or infusion (intravenous, intramuscular, intraperitoneal or subcutaneous) over the course of treatment. Antibodies are generally administered in an amount suficient to provide a minimum circulating level of antibody throughout the treatment period of between approximately 20 µg and 1 mg/kg body weight. In this regard, it is preferred to use antibodies having a circulating half-life of at least 12 hours, preferably at least 4 days, more preferably up to 14–21 days. Chimeric and humanized antibodies are expected to have circulatory half-lives of up to four and up to 14–21 days, respectively. In many cases it will be preferable to administer daily doses during a hospital stay, followed by less frequent bolus injections during a period of outpatient treatment. Antibodies can also be delivered by slow-release delivery systems, pumps, and other known delivery systems for continuous infusion. Dosing regimens may be varied to provide the desired circulating levels of a particular antibody based on its pharmacokinetics. Thus, doses will be calculated so that the desired circulating level of therapeutic agent is maintained. Daily doses referred to above may be administered as larger, less frequent bolus administrations to provide the recited dose averaged over the term of administration.

Those skilled in the art will recognize that the same principles will guide the use of other zvegf3 antagonists. The dosing regimen for a given antagonist will be determined by a number of factors including potency, pharmacokinetics, and the physicochemical nature of the antagonist. For example, non-peptidic zvegf3 antagonists may be administered enterally.

Therapeutic polynucleotides, such as antisense polynucleotides, can be delivered to patients or test animals by way of viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161–89, 1994; and Douglas and Curiel, *Science & Medicine* 4:4453, 1997. The adenovirus system offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., *J. Biol. Chem.* 263:14621–14624, 1988; Wu et al., *J. Biol. Chem.* 267:963–967, 1992; and Johnston and Tang, *Meth. Cell Biol.* 43:353–365, 1994.

Activity of zvegf3 antagonists can be measured in vitro using assays (including cell-based assays) designed to measure zvegf3 activity. Antagonists will reduce the effects of zvegf3 within the assay. Ligand-receptor binding can be assayed by a variety of methods well known in the art, including receptor competition assays (Bowen-Pope and Ross, *Methods Enzymol.* 109:69–100, 1985) and through the use of soluble receptors, including receptors produced as IgG fusion proteins (U.S. Pat. No. 5,750,375). Receptor binding assays can be performed on cell lines that contain known cell-surface receptors for evaluation. The receptors can be naturally present in the cell, or can be recombinant receptors expressed by genetically engineered cells. Mitogenic activity can be measured using known assays, including $^3$H-thymidine incorporation assays (as disclosed by, e.g., Raines and Ross, *Methods Enzymol.* 109:749–773, 1985 and Wahl et al., *Mol. Cell Biol.* 8:5016–5025, 1988), dye incorporation assays (as disclosed by, for example, Mosman, *J. Immunol. Meth.* 65:55–63, 1983 and Raz et al., *Acta Trop.* 68:139–147, 1997) or cell counts. Suitable mitogenesis assays measure incorporation of $^3$H-thymidine into (1) 20% confluent cultures to look for the ability of zvegf3 proteins to further stimulate proliferating cells, and (2) quiescent cells held at confluence for 48 hours to look for the ability of zvegf3 proteins to overcome contact-induced growth inhibition. Suitable dye incorporation assays include measurement of the incorporation of the dye Alamar blue (Raz et al., ibid.) into target cells. See also, Gospodarowicz et al., *J. Cell. Biol.* 70:395405, 1976; Ewton and Florini, *Endocrinol.* 106:577–583, 1980; and Gospodarowicz et al., *Proc. Natl. Acad. Sci. USA* 86:7311–7315, 1989.

The biological activities of zvegf3 antagonists can be studied in non-human animals by administration of exogenous compounds, by expression of zvegf3 antisense polynucleotides, and by suppression of endogenous zvegf3 expression through knock/out techniques. Viral delivery systems (disclosed above) can be employed. Zvegf3 antagonists can be administered or expressed individually, in combination with other zvegf3 antagonists, or in combination other compounds, including other growth factor antagonists. Test animals are monitored for changes in such parameters as clinical signs, body weight, blood cell counts, clinical chemistry, histopathology, and the like.

Effects of zvegf3 antagonists on liver and kidney fibrosis can be tested in known animal models, such as the db/db mouse model disclosed by Cohen et al., *Diabetologia* 39:270–274, 1996 and Cohen et al., *J. Clin. Invest.* 95:2338–2345, 1995, transgenic animal models (Imai et al., *Contrib. Nephrol.* 107:205–215, 1994), and the $CCl_4$-induced cirrhosis model (Rojkind and Greenwel, *Adv. Vet. Sci. Comp. Med.* 37:333–355, 1993; Diaz-Gil et al., *J. Hepatol.* 30:1065–1072, 1999).

Effects on lung fibrosis can be assayed in a mouse model using bleomycin. The chemotherapy agent bleomycin is a known causative agent of pulmonary fibrosis in humans and can induce interstitial lung disease in mice, including an increase in the number of fibroblasts, enhanced collagen deposition, and dysregulated matrix remodeling. C57Bl/6 mice are administered bleomycin by osmotic minipump for 1 week. There follows a period of inflammation, with cutaneous toxicity beginning approximately 4–7 days after bleomycin administration and continuing for about a week, after which the mice appear to regain health. About 3–4 weeks after the finish of bleomycin delivery, the mice are sacrificed, and the lungs are examined histologically for signs of fibrosis. Scoring is based on the extent of lung fibrotic lesions and their severity. Serum is assayed for lactic dehydrogenase, an intracellular enzyme that is released into the circulation upon general cell death or injury. Lung tissue is assayed for hydroxyproline as a measure of collagen deposition.

The invention is further illustrated by the following non-limiting examples.

EXAMPLES

Example 1

A human salivary gland library was screened for a full-length clone of zvegf3 by PCR. This library was an arrayed library representing $9.6 \times 10^5$ clones made in the vector pZPSx. The vector pZP5x is the same as vector pZP-9 (deposited with American Type Culture Collection, 10801 University Blvd., Manassas, Va. under Accession Number 98668), but contains a cytomegalovirus promoter instead of a metallothionein promoter between the Asp718 and BamHI sites. The plasmid thus comprises a dihyrofolate reductase gene under control of the SV40 early promoter and SV40 polyadenylation site, and a cloning site to insert the gene of interest under control of the CMV promoter and the human growth hormone (hGH) gene polyadenylation site. The working plate containing 80 pools of 12,000 colonies each was screened by PCR using oligonucleotide primers ZC19, 045 (SEQ ID NO:6) and ZC19,047 (SEQ ID NO:7) with an annealing temperature of 60° C. for 35 cycles. There were two strong positives, pools 58 (T-8 F1–F12) and 77 (T-7 H1–H12). The corresponding pools in the transfer plate were then screened by PCR using the same conditions. Two positives were obtained at the transfer level. The positives were T-7H11 and T-8 F10. 5' RACE reactions were done on the transfer plate pools, and the fragments were sequenced to check zvegf3 sequence and determine if a full-length clone was present. For PCR, oligonucleotide primers ZC12, 700 (SEQ ID NO:8) and ZC19,045 (SEQ ID NO:6) were used at an annealing temperature of 61° C. for 5 cycles, then 55° C. for 30 cycles. Sequencing showed that the pool T-7H 11 had a frameshift. Transfer plate 8 pool F10 sequence appeared to be correct, so this pool of DNA was used in filter lifts.

Pool F10 from transfer plate 8 was plated and filter lifted using nylon membranes (Hybond-N™; Amersham Corporation). Approximately 1200 colonies per plate on each of 5 filters were lifted for a total of approximately 6000 colonies. The filters were marked with a hot needle for orientation, then denatured for 6 minutes in 0.5 M NaOH and 1.5 M Tris-HCl, pH 7.2. The filters were then neutralized in 1.5 M NaCl and 0.5 M Tris-HCl, pH 7.2 for 6 minutes. The DNA was affixed to the filters using a UV crosslinker (Stratalinker®, Stratagene, La Jolla, Calif.) at 1200 joules. The filters were prewashed at 65° C. in prewash buffer consisting of 0.25×SSC, 0.25% SDS, and 1 mM EDTA. The solution was changed a total of three times over a 45-minute period to remove cell debris. Filters were prehybridized for approximately 3 hours at 65° C. in 25 ml of ExpressHyb™. The probe was generated using an approximately 400-bp fragment produced by digestion of the first proprietary database clone with EcoRI and BglII and gel-purified using a spin column as disclosed above. The probe was radioactively labeled with $^{32}$P by random priming as disclosed above and purified using a push column. ExpressHyb™ solution was used for the hybridizing solution for the filters. Hybridization took place overnight at 65° C. Blots were rinsed 2× in 65° C. solution 1 (2×SSC, 0.1% SDS), then washed 4 times in solution 1 at 65° C. The filters were exposed to film overnight at −80° C. There were 14 positives on the filters. 85 clones were picked from the positive areas and screened by PCR using oligonucleotide primers ZC19,045 (SEQ ID NO:6) and ZC19,047 (SEQ ID NO:7) and an annealing temperature of 60° C. Thirteen positives were obtained and streaked out for individual clones. Twenty-four colonies were picked and checked by PCR as previously described. Six positives were obtained, two of which were sequenced. Both sequences were the same and full length. The sequence is shown in SEQ ID NO:1.

Example 2

A PCR panel was screened for mouse zvegf3 DNA. The panel contained 8 cDNA samples from brain, bone marrow, 15-day embryo, testis, salivary gland, placenta, 15-day embryo (Clontech Laboratories), and 17-day embryo (Clontech Laboratories) libraries.

PCR mixtures contained oligonucleotide primers ZC21, 222 (SEQ ID NO:9) and ZC21,224 (SEQ ID NO: 10). The reaction was run at an annealing temperature of 66° C. with an extension time of 2 minutes for a total of 35 cycles using Ex Taq™ DNA polymerase (Pan Vera, Madison, Wis.) plus antibody. DNA samples found to be positive for zvegf3 by PCR and confirmed by sequencing included mouse 15-day embryo library total pool cDNA, mouse 15-day embryo (Clontech Laboratories) and 17-day embryo (both obtained from Clontech Laboratories), mouse salivary gland library total pool cDNA, and mouse testis library total pool cDNA. Fragments of about 600 bp from each of the mouse 15-day embryo library total pool cDNA, mouse 15-day embryo mcDNA, and mouse 17-day embryo mcDNA PCR products were sequenced. Sequence from the mouse 17-day embryo mcDNA and mouse 15-day embryo library total pool cDNA products confirmed the fragments to be mouse zvegf3 DNA.

The mouse 15-day embryo library was screened for full-length zvegf3 DNA. This library was an arrayed library representing 9.6×10$^5$ clones in the pCMV·SPORT 2 vector (Life Technologies, Gaithersburg, Md.). The working plate, containing 80 pools of 12,000 colonies each, was screened by PCR using oligonucleotide primers ZC21,223 (SEQ ID NO:1) and ZC21,224 (SEQ ID NO:10) with an annealing temperature of 66° C. for 35 cycles. Eighteen positives were obtained. Fragments from four pools (A2, A10, B2, and C4) were sequenced; all were confirmed to encode zvegf3. Additional rounds of screening using the same reaction conditions and pools from the working and source plates identified one positive pool (5D).

Positive colonies were screened by hybridization. Pool 5D from original source plate #5 was plated at about 250 colonies per plate and transferred to nylon membranes (Hybond-N™; Amersham Corporation, Arlington Heights, Ill.). Five filters were lifted for a total of ~1250 colonies. The filters were marked with a hot needle for orientation, then denatured for 6 minutes in 0.5 M NaOH and 1.5 M Tris-HCl, pH 7.2. The filters were then neutralized in 1.5 M NaCl and 0.5 M Tris-HCl, pH 7.2 for 6 minutes. The DNA was fixed to the filters using a a UV crosslinker (Stratalinker®, Stratagene, La Jolla, Calif.) at 1200 joules. A probe was generated by PCR using oligonucleotide primers ZC21,223 (SEQ ID NO:11) and ZC21,224 (SEQ ID NO:10), and a mouse 15-day embryo template at an annealing temperature of 66° C. for 35 cycles. The PCR fragment was gel purified using a spin column containing a silica gel membrane (QIAquick™ Gel Extraction Kit; Qiagen, Inc., Valencia, Calif.). The DNA was radioactively labeled with $^{32}$P using a commercially available kit (Rediprime™ II random-prime labeling system; Amersham Corp., Arlington Heights, Ill.) according to the manufacturer's specifications. The probe was purified using a commercially available push column (NucTrap® column; Stratagene, La Jolla, Calif.; see U.S. Pat. No. 5,336,412). The filters were prewashed at 65° C. in prewash buffer consisting of 0.25×SSC, 0.25% SDS and 1 nmM EDTA. The solution was changed a total of three times over a 45-minute period to remove cell debris. Filters were prehybridized overnight at 65° C. in 25 ml of a hybridization solution (ExpressHyb™ Hybridization Solution; Clontech Laboratories, Inc., Palo Alto, Calif.), then hybridized overnight at 65° C in the same solution. Filters were rinsed twice at 65° C. in pre-wash buffer (0.25×SSC, 0.25% SDS, and 1 mM EDTA), then washed twice in pre-wash buffer at 65° C. Filters were exposed to film for 2 days at −80° C. There were 10 positives on the filters. 3 clones were picked from the positive areas, streaked out, and 15 individual colonies from these three positives were screened by PCR using primers ZC21,223 (SEQ ID NO:1) and ZC21,334 (SEQ ID NO: 12) at an annealing temp of 66° C. Two positives were recovered and sequenced. Both sequences were found to be the same and encoded full-length mouse zvegf3 (SEQ ID NO:4).

The amino acid sequence is highly conserved between mouse and human zvegf3s, with an overall amino acid sequence identity of 87%. The secretory peptide, CUB domain, inter-domain, and growth factor domain have 82%, 92%, 79% and 94% amino acid identity, respectively.

Example 3

A mammalian cell expression vector for the growth factor domain of zvegf3 was constructed by joining the zvegf3 fragment to a sequence encoding an optimized t-PA secretory signal sequence (U.S. Pat. No. 5,641,655) in the linearized pZMP11 vector downstream of the CMV promoter. The plasmid pZMP11 is a mammalian expression vector containing an expression cassette having the CMV immediate early promoter, a consensus intron from the variable region of mouse immunoglobulin heavy chain locus, Kozak sequences, multiple restriction sites for insertion of coding sequences, a stop codon, and a human growth hormone terminator. The plasmid also contains an IRES element from poliovirus, the extracellular domain of CD8 truncated at the C-terminal end of the transmembrane domain, an E. coli origin of replication, a mammalian selectable marker expression unit having an SV40 promoter, enhancer and origin of replication, a DHFR gene, the SV40 terminator, and the URA3 and CEN-ARS sequences required for selection and replication in S. cerevisiae. The resulting vector was designated pZMP11/zv3GF-otPA.

BHK 570 cells were transfected with pZMP11 zv3GF-otPA by liposome-mediated transfection (using (Lipofectamine™; Life Technologies) and cultured according to conventional procedures.

BHK cell-conditioned media was adjusted to 20 mM MES at pH 5.5. A column of cation exchange resin (Poros® HS 50; PerSeptive Biosystems, Framingham, Mass.) (2-cm diameter; 50 ml bed volume) was equilibrated in 20 mM MES, 150 mM NaCl, pH 5.5. The adjusted media was pumped into the column at 20 ml/minute. When loading was completed, the column was washed, first in 20 mM MES, 150 μM NaCl, pH 5.5, then with the same composition buffer at pH 6.0. Once the baseline was back to zero absorbance, the column was eluted with a 10 column volume gradient to 20 mM MES, 1M NaCl, pH 6.0. The zvegf3 growth factor domain eluted at 25 to 50 mS conductivity during the evolving gradient. Reducing SDS-PAGE revealed a distinct band at 20 kD, which was confirmed as zvegf3 by Western blotting. This material was pooled and prepared for loading to a tandem column array comprising a strong anion exchange resin (Poros® HQ 50; PerSeptive Biosystems) followed by an immobilized metal (nickel) affinity column in series. The system of columns was equilibrated in 20 mM MOPS buffer at pH 7.0. The vegf3 pool was in-line diluted at 1:10 (V:V) with the MOPS equilibration buffer while loading. After loading was completed the column series was washed with 20 mM MOPS pH 7.0 buffer until baseline absorbance was obtained. The nickel column was then disconnected from the anion exchanger and washed with 20 mM MOPS pH 7.0 containing 150 mM NaCl. The column was then eluted with a 1 column volume gradient between the last washing buffer and the same buffer containing 20 mM imidazole at pH 7.0. The fractions containing the zvegf3 growth factor domain were pooled and concentrated using 5 kD cuttoff membrane in preparation for buffer exchange and polishing on a size exclusion column equilibrated in PBS.

Example 4

To make transgenic animals expressing zvegf3 genes requires adult, fertile males (studs) (B6C3f1, 2–8 months of age (Taconic Farms, Germantown, N.Y.)), vasectomized males (duds) (B6D2f1, 2–8 months, (Taconic Farms)), pre-pubescent fertile females (donors) (B6C3f1, 4–5 weeks, (Taconic Farms)) and adult fertile females (recipients) (B6D2f1, 2–4 months, (Taconic Farms)).

The donors are acclimated for 1 week, then injected with approximately 8 IU/mouse of Pregnant Mare's Serum gonadotrophin (Sigma, St. Louis, Mo.) I.P., and 46–47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope (Leica MZ12 Stereo Microscope, Leica, Wetzlar, Germany). The oviducts are collected and eggs are released into urinanalysis slides containing hyaluronidase (Sigma Chemical Co.). Eggs are washed once in hyaluronidase, and twice in Whitten's W640 medium (Table 2; all reagents available from Sigma Chemical Co.) that has been incubated with 5% $CO_2$, 5% $O_2$, and 90% $N_2$ at 37° C. The eggs are stored in a 37° C./5% $CO_2$ incubator until microinjection.

TABLE 2

|  | mgs/200 ml | mgs/500 ml |
| --- | --- | --- |
| NaCl | 1280 | 3200 |
| KCl | 72 | 180 |
| $KH_2PO_4$ | 32 | 80 |
| $MgSO_4.7H_2O$ | 60 | 150 |
| Glucose | 200 | 500 |
| $Ca^{2+}$ Lactate | 106 | 265 |
| Benzylpenicillin | 15 | 37.5 |
| Streptomycin $SO_4$ | 10 | 25 |
| $NaHCO_3$ | 380 | 950 |
| Na Pyruvate | 5 | 12.5 |
| $H_2O$ | 200 ml | 500 ml |
| 500 mM EDTA | 100 µl | 250 µl |
| 5% Phenol Red | 200 µl | 500 µl |
| BSA | 600 | 1500 |

Zvegf3 cDNA is inserted into the expression vector pHB12-8. Vector pHB12-8 was derived from p2999B4 (Palmiter et al., *Mol. Cell Biol.* 13:5266–5275, 1993) by insertion of a rat insulin II intron (ca. 200 bp) and polylinker (Fse I/Pme I/Asc I) into the Nru I site. The vector comprises a mouse metallothionein (MT-1) promoter (ca. 750 bp) and human growth hormone (hGH) untranslated region and polyadenylation signal (ca. 650 bp) flanked by 10 kb of MT-I 5' flanking sequence and 7 kb of MT-I 3' flanking sequence. The cDNA is inserted between the insulin II and hGH sequences.

10–20 micrograms of plasmid DNA is linearized, gel-purified, and resuspended in 10 mM Tris pH 7.4, 0.25 mM EDTA pH 8.0, at a final concentration of 5–10 nanograms per microliter for microinjection.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary) and injected into individual eggs. Each egg is penetrated with the injection needle into one or both of the haploid pronuclei.

Picoliters of DNA are injected into the pronuclei, and the injection needle is withdrawn without coming into contact with the nucleoli. The procedure is repeated until all the eggs are injected. Successfully microinjected eggs are transferred into an organ tissue-culture dish with pregassed W640 medium for storage overnight in a 37° C./5% $CO_2$ incubator.

The following day, 2-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12–17 healthy 2-cell embryos from the previous day's injection are transferred into the recipient. The swollen ampulla is located and holding the oviduct between the ampulla and the bursa, and a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs are allowed to slide in. The peritoneal wall is closed with one suture, and the skin is closed with a wound clip. The mice recuperate on a 37° C. slide warmer for a minimum of 4 hours.

The recipients are returned to cages in pairs, and allowed 19–21 days gestation. After birth, 19–21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using a commercially available kit (DNeasy™ 96 Tissue Kit; Qiagen, Valencia, Calif.) following the manufacturer's instructions. Genomic DNA is analyzed by PCR using primers designed to the human growth hormone (hGH) 3' UTR portion of the transgenic vector. The use of a region unique to the human sequence (identified from an alignment of the human and mouse growth hormone 3' UTR DNA sequences) ensures that the PCR reaction does not amplify the mouse sequence. Primers ZC17,251 (SEQ ID NO:13) and ZC17,252 (SEQ ID NO:14) amplify a 368-base-pair fragment of hGH. In addition, primers ZC17,156 (SEQ ID NO:15) and ZC17,157 (SEQ ID NO:16), which hybridize to vector sequences and amplify the cDNA insert, may be used along with the hGH primers. In these experiments, DNA from animals positive for the transgene will generate two bands, a 368-base-pair band corresponding to the hGH 3' UTR fragment and a band of variable size corresponding to the cDNA insert.

Once animals are confirmed to be transgenic (TG), they are back-crossed into an inbred strain by placing a TG female with a wild-type male, or a TG male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the xiphoid process. Using sterile technique, a small 1.5–2 cm incision is made below the sternum, and the left lateral lobe of the liver is exteriorized. Using 4-0 silk, a tie is made around the lower lobe securing it outside the body cavity. An atraumatic clamp is used to hold the tie while a second loop of absorbable Dexon (American Cyanamid, Wayne, N.J.) is placed proximal to the first tie. A distal cut is made from the Dexon tie, and approximately 100 mg of the excised liver tissue is placed in a sterile petri dish. The excised liver section is transferred to a 14-ml polypropylene round bottom tube, snap frozen in liquid nitrogen, and stored on dry ice. The surgical site is closed with suture and wound clips, and the animal's cage is placed on a 37° C. heating pad for 24 hours post-operatively. The animal is checked daily post-operatively, and the wound clips are removed 7–10 days after surgery.

Analysis of the mRNA expression level of each transgene is done using an RNA solution hybridization assay or real-time PCR on an ABI Prism 7700 (PE Applied Biosystems, Inc., Poster City, Calif.) following the manufacturer's instructions.

An adenovirus vector was prepared using a liver-specific albumin gene enhancer and basal promoter (designated "AEO promoter"). The albumin promoter construct (designated pAEO) was constructed by inserting a 2.2 kb NotI/EcoRV fragment from pALBdelta2L (Pinkert et al., Genes Dev. 1:268–276, 1987) and an 850 bp NruI/Not1 DNA segment comprising the rat insulin II intron, an FseI/PmeI/AscI polylinker, and the human growth hormone poly A sequence into a commercially available phagemid vector (pBluescript® KS(+); Stratagene, La Jolla, Calif.). For microinjection, the plasmid is digested with Not1 to liberate the expression cassette.

An additional adenovirus vector was constructed using an epithelial cell-specific keratin gene (K14) promoter (Vassar et al., Proc. Natl. Acad. Sci. USA 86:1563–1567, 1989). The 1038-bp open reading frame encoding full-length human zvegf3 was amplified by PCR so as to introduce an optimized initiation codon and flanking 5' PmeI and 3' AscI sites using the primers ZC20,180 (SEQ ID NO:17) and ZC20,181 (SEQ ID NO: 18). The resulting PmeI/AscI fragment was subcloned into the polylinker of pKF0114, a basal keratinocyte-restricted transgenic vector comprising the human keratin 14 (K14) promoter (an approximately 2.3 Kb fragment amplified from human genomic DNA [obtained from Clontech Laboratories, Inc.] based on the sequence of Staggers et al., "Sequence of the promoter for the epidermal keratin gene, K14", GenBank accession #U11076, 1994), followed by a heterologous intron (a 294 bp bp BstXI/PstI fragment from pIRES1hyg (Clontech Laboratories, Inc.; see, Huang and Gorman, Nucleic Acids Res. 18:937–947, 1990), a PmeI/AscI polylinker, and the human growth hormone gene polyadenylation signal (a 627 bp SmaI/EcoRI fragment; see, Seeburg, DNA 1:239–249, 1982). The transgene insert was separated from the plasmid backbone by NotI digestion and agarose gel purification, and fertilized ova from matings of B6C3F1 Tac mice or inbred FVB/NTac mice were microinjected and implanted into pseudopregnant females essentially as described by Malik et al., Molec. Cell. Biol. 15:2349–2358, 1995. Transgenic founders were identified by PCR on genomic tail DNA using primers specific for the human growth hormone poly A signal (ZC17,252, SEQ ID NO:14; and ZC17,251, SEQ ID NO:13) to amplify a 368-bp diagnostic product. Transgenic lines were initiated by breeding founders with C57BL/6Tac or FVB/NTac mice.

Transgenic mice were generated essentially as disclosed above using MT-1, K14, and AEO promoters. Four MT-1/zvegf3 transgenic mice were generated. In one animal (female) approximately 800 molecules zvegf3 mRNA/cell were produced in the liver after zinc induction. This animal had enlargement of the liver and spleen. Also observed were proliferation of hepatic sinusoidal cells and extra-medullary hematopoiesis. One K14/zvegf3 transgenic mouse (female) showed a low level of expression with low body weight, low hematocrit, and low platelet count. One AEO/zvegf3 transgenic mouse (male) with a low level of expression exhibited liver sinusoidal cell proliferation.

Histological analysis was carried out on livers from N1 transgenic mice overexpressing full-length zvegf3 from the AEO promoter and nontransgenic littermate controls at 8, 16, 22, and 33 weeks of age. Similar changes were seen in male and female animals. H & E and trichrome stains indicate a definite increase in number of liver sinusoidal (stellate) cells and increased perisinusoidal extracellular matrix (EMC) deposition at 8 weeks of age. There was a persistent increase in number of stellate cells and in the amount and thickness of perisinusoidal EMC as well as some perivenular EMC deposition by 16 weeks. At 22 weeks similar changes were seen, but with an increase in incidence and severity of perivenular fibrosis (steato fibrosis). Changes similar to those at 16 and 22 weeks were observed at 33 weeks, however some animals had fibrotic banding and multiple, encapsulated areas in which hepatocytes appeared enlarged and vacuolated. These areas tended to be surrounded by a fibrous tissue capsule, and the hepatocytes within these areas appeared normal. These changes were consistent with early cirrhosis.

Similar changes were seen in 8-week-old N2 mice and in breeder males sacrificed at approximately 32–34 weeks.

Example 5

For construction of adenovirus vectors, the protein coding region of human zvegf3 was amplified by PCR using primers that added PmeI and AscI restriction sties at the 5' and 3' termini respectively. PCR primers ZC20,180 (SEQ ID NO:17) and ZC20,181 (SEQ ID NO:18) were used with a full-length zvegf3 cDNA template in a PCR reaction as follows: incubation at 95° C. for 5 minutes; followed by 15 cycles at 95° C. for 1 nin., 61° C. for 1 min., and 72° C. for 1.5 min.; followed by 72° C. for 7 min.; followed by a 4° C. soak. The reaction product was loaded onto a 1.2% low-melting-temperature agarose gel in TAE buffer (0.04 M Tris-acetate, 0.001M EDTA). The zvegf3 PCR product was excised from the gel and purified using a commercially available kit comprising a silica gel mambrane spin column (QIAquick™ PCR Purification Kit and gel cleanup kit; Qiagen, Inc.) as per kit instructions. The zvegf3 product was then digested with PmeI and AscI, phenol/chloroform extracted, EtOH precipitated, and rehydrated in 20 ml TE (Tris/EDTA pH 8). The 1038 bp zvegf3 fragment was then ligated into the PmeI-AscI sites of the transgenic vector pTG12-8 (also known as pHB12-8; see Example 4) and transformed into E. Coli DH10B™ competent cells by electroporation. Clones containing zvegf3 were identified by plasmid DNA miniprep followed by digestion with PmeI and AscI. A positive clone was sequenced to insure that there were no deletions or other anomalies in the construct. The sequence of zvegf3 cDNA was confirmed.

DNA was prepared using a commercially available kit (Maxi Kit, Qiagen, Inc.), and the 1038 bp zvegf3 cDNA was released from the pTG12-8 vector using PmeI and AscI enzymes. The cDNA was isolated on a 1% low melting temperature agarose gel and was excised from the gel. The gel slice was melted at 70° C., and the DNA was extracted twice with an equal volume of Tris-buffered phenol and precipitated with EtOH. The DNA was resuspended in 10 μl $H_2O$.

The zvegf3 cDNA was cloned into the EcoRV-AscI sites of a modified pAdTrack-CMV (He, T-C. et al., Proc. Natl. Acad. Sci. USA 95:2509–2514, 1998). This construct contains the green fluorescent protein (GFP) marker gene. The CMV promoter driving GFP expression was replaced with the SV40 promoter, and the SV40 polyadenylation signal was replaced with the human growth hormone polyadenylation signal. In addition, the native polylinker was replaced with FseI, EcoRV, and AscI sites. This modified form of pAdTrack-CMV was named pZyTrack. Ligation was performed using a commercially available DNA ligation and screening kit (Fast-Link™ kit; Epicentre Technologies, Madison, Wis.). Clones containing zvegf3 were identified by digestion of mini prep DNA with FseI and AscI. In order to linearize the plasmid, approximately 5 μg of the resulting pZyTrack zvegf3 plasmid was digested with PmeI. Approximately 1 μg of the linearized plasmid was cotransformed with 200 ng of supercoiled pAdEasy (He et al., ibid.) into E. coli BJ5183 cells (He et al., ibid.). The co-transformation was done using a Bio-Rad Gene Pulser at 2.5 kV, 200 ohms and 25 μFa. The entire co-transformation mixture was plated on 4 LB plates containing 25 μg/ml kanamycin. The smallest colonies were picked and expanded in LB/kanamycin, and recombinant adenovirus DNA was identified by standard DNA miniprep procedures. Digestion of the recombinant adenovirus DNA with FseI and AscI confirmed the presence of the zvegf3 insert. The recombinant adenovirus miniprep DNA was transformed into E. coli DH10B™ competent cells, and DNA was prepared using a Maxi Kit (Qiagen, Inc.) according to kit instructions.

Approximately 5 μg of recombinant adenoviral DNA was digested with PacI enzyme (New England Biolabs) for 3 hours at 37° C. in a reaction volume of 100 μl containing 20–30U of PacI. The digested DNA was extracted twice with an equal volume of phenol/chloroform and precipitated with ethanol. The DNA pellet was resuspended in 10 μl distilled water. A T25 flask of QBI-293A cells (Quantum Biotechnologies, Inc. Montreal, Qc. Canada), inoculated the day before and grown to 60–70% confluence, were transfected with the PacI digested DNA. The PacI-digested DNA was diluted up to a total volume of 50 μl with sterile HBS (150 mM NaCl, 20 mM HEPES). In a separate tube, 20 μl of 1 mg/ml N-[1-(2,3-Dioleoyloxy)propyl]-N,N,N-trimethyl-ammonium salts (DOTAP) (Boehringer Mannheim, Indianapolis, Ind.) was diluted to a total volume of 100 μl with HBS. The DNA was added to the DOTAP, mixed gently by pipeting up and down, and left at room temperature for 15 minutes. The media was removed from the 293A cells and washed with 5 ml serum-free minimum essential medium (MEM) alpha containing 1 nM sodium pyruvate, 0.1 mM MEM non-essential amino acids, and 25 mM HEPES buffer (reagents obtained from Life Technologies, Gaithersburg, Md.). 5 ml of serum-free MEM was added, and the cells were held at 37° C. The DNA/lipid mixture was added drop-wise to the flask of cells, mixed gently, and incubated at 37° C. for 4 hours. The media containing the DNA/lipid mixture was then aspirated off and replaced with 5 ml complete MEM containing 5% fetal bovine serum. The transfected cells were monitored for GFP expression and formation of foci (viral plaques).

Seven days after transfection of 293A cells with the recombinant adenoviral DNA, the cells expressed GFP and started to form foci. The crude viral lysate was collected using a cell scraper to collect all of the 293A cells. The lysate was transferred to a 50-ml conical tube. To release most of the virus particles from the cells, three freeze/thaw cycles were done in a dry ice/ethanol bath and a 37° waterbath.

The crude lysate was amplified (Primary (1°) amplification) to obtain a working stock of zvegf3 rAdV lysate. Ten 10-cm plates of nearly confluent (80–90%) 293A cells were set up 20 hours previously, 200 μl of crude rAdV lysate added to each 10-cm plate and monitored for 48 to 72 hours looking for CPE under the white light microscope and expression of GFP under the fluorescent microscope. When all of the cells showed CPE (Cytopathic Effect) this 1° stock lysate was collected and freeze/thaw cycles performed as described above.

Secondary (20) amplification of zvegf3 rAdV was obtained as follows: Twenty 15-cm tissue culture dishes of 293A cells were prepared so that the cells were 80–90% confluent. All but 20 ml of 5% MEM media was removed, and each dish was inoculated with 300–500 μl of the 1° amplified rAdv lysate. After 48 hours the cells were lysed from virus production, the lysate was collected into 250 ml polypropylene centrifuge bottles, and the rAdV was purified.

NP-40 detergent was added to a final concentration of 0.5% to the bottles of crude lysate in order to lyse all cells. Bottles were placed on a rotating platform for 10 minutes agitating as fast as possible without the bottles falling over. The debris was pelleted by centrifugation at 20,000×G for 15 minutes. The supernatant was transferred to 250-ml polycarbonate centrifuge bottles, and 0.5 volume of 20% PEG8000/2.5 M NaCl solution was added. The bottles were shaken overnight on ice. The bottles were centrifuged at 20,000×G for 15 minutes and, the supernatant was discarded into a bleach solution. Using a sterile cell scraper, the white, virus/PEG precipitate from 2 bottles was resuspended in 2.5 ml PBS. The resulting virus solution was placed in 2-ml microcentrifuge tubes and centrifuged at 14,000×G in the microcentrifuge for 10 minutes to remove any additional cell debris. The supernatant from the 2-ml microcentrifuge tubes was transferred into a 15-ml polypropylene snapcap tube and adjusted to a density of 1.34 g/ml with CsCl. The volume of the virus solution was estimated, and 0.55 g/ml of CsCl was added. The CsCl was dissolved, and 1 ml of this solution weighed 1.34 g. The solution was transferred to 3.2-ml, polycarbonate, thick-walled centrifuge tubes and spun at 348,000×G for 3–4 hours at 25° C. The virus formed a white band. Using wide-bore pipette tips, the virus band was collected.

The virus recovered from the gradient had a large amount of CsCl which had to be removed before it was used on cells. Commercially available ion-exchange columns (PD-10 columns prepacked with Sephadex® G-25M; Pharmacia Biotech, Piscataway, N.J.) were used to desalt the virus preparation. The column was equilibrated with 20 ml of PBS. The virus was loaded and allowed to run into the column. 5 ml of PBS was added to the column, and fractions of 8–10 drops were collected. The optical density of a 1:50 dilution of each fraction was determined at 260 mm on a spectrophotometer. A clear absorbance peak was present between fractions 7–12. Peak fractions were pooled, and the optical density (OD) of a 1:25 dilution was determined. OD was converted to virus concentration using the formula: (OD at 260 nm)(25)(1.1×10$^{12}$)=virions/ml. The OD of a 1:25 dilution of the zvegf3 rAdV was 0.145, giving a virus concentration of 4×10$^2$ virions/ml.

To store the virus, glycerol was added to the purified virus to a final concentration of 15%, mixed gently but effectively, and stored in aliquots at −80° C.

A protocol developed by Quantum Biotechnologies, Inc. (Montreal, Canada) was followed to measure recombinant virus infectivity. Briefly, two 96-well tissue culture plates were seeded with $1\times10^4$ 293A cells per well in MEM containing 2% fetal bovine serum for each recombinant virus to be assayed. After 24 hours 10 fold dilutions of each virus from $1\times10^{-2}$ to $1\times10^{-14}$ were made in MEM containing 2% fetal bovine serum. 100 μl of each dilution was placed in each of 20 wells. After 5 days at 37° C., wells were read either positive or negative for Cytopathic Effect (CPE), and a value for plaque forming units (pfu)/ml was calculated.

$TCID_{50}$ formulation used was as per Quantum Biotechnologies, Inc., above. The titer (T) was determined from a plate where virus was diluted from $10^{-2}$ to $10^-14$, and read 5 days after the infection. At each dilution a ratio (R) of positive wells for CPE per the total number of wells was determined.

To calculate titer of the undiluted virus sample: the factor, "F"=1+d(S0.5); where "S" is the sum of the ratios (R); and "d" is Log 10 of the dilution series, for example, "d" is equal to 1 for a ten-fold dilution series. The titer of the undiluted sample is $T=10^{(1+F)}=TCID_{50}$/ml. To convert $TCID_{50}$/ml to pfu/ml, 0.7 is subtracted from the exponent in the calculation for titer (T).

The zvegf3 adenovirus had a titer of $1.8\times10^{10}$ pfu/ml.

Example 6

Treatment of mice with zvegf3-adenovirus led to changes in liver and spleen. The livers were pale and very enlarged, with enlarged vessels at the tips of the lobes. The livers also showed sinusoidal cell proliferation. Changes were also seen in hepatocytes (hypertrophy, degeneration, and necrosis) and were most likely non-specific effects of adenovirus infection. Splenic change consisted of increased extramedullary hematopoiesis, which was correlated with enlarged splenic size.

Example 7

Polyclonal anti-peptide antibodies were prepared by immunizing two female New Zealand white rabbits with the peptides huzvegf3-1 (residues 80–104 of SEQ ID NO:2), huzvegf3-2 (residues 299–314 of SEQ ID NO:2), huzvegf3-3 (residues 299–326 of SEQ ID NO:2 with an N-terminal cys residue), or huzvegf34 (residues 195–225 of SEQ ID NO:2 with a C-terminal cys residue). The peptides were synthesized using an Applied Biosystems Model 431A peptide synthesizer (Applied Biosystems, Inc., Foster City, Calif.) according to the manufacturer's instructions. The peptides huzvegf3-1, huzvegf3-3, and huzvegf34 were then conjugated to the carrier protein maleimide-activated keyhole limpet hemocyanin (KLH) through cysteine residues (Pierce Chemical Co., Rockford, Ill.). The peptide huzvefg3-2 was conjugated to the carrier protein KLH using gluteraldehyde. The rabbits were each given an initial intraperitoneal (IP) injection of 200 μg of conjugated peptide in Complete Freund's Adjuvant (Pierce Chemical Co.) followed by booster IP injections of 100 μg conjugated peptide in Incomplete Freund's Adjuvant every three weeks. Seven to ten days after the administration of the third booster injection, the animals were bled and the serum was collected. The rabbits were then boosted and bled every three weeks.

The huzvegf3 peptide-specific antibodies were affinity purified from the rabbit serum using an CNBr—Sepharose® 4B peptide column (Pharmacia Biotech) that was prepared using 10 mg of the respective peptides per gram CNBr—Sepharose®, followed by dialysis in PBS overnight. Peptide specific-huzvegf3 antibodies were characterized by an ELISA titer check using 1 μg/ml of the appropriate peptide as an antibody target. The huzvegf3-1 peptide-specific antibodies had a lower limit of detection (LLD) of 500 pg/ml by ELISA on the appropriate antibody target and recognize full-length recombinant protein (MBP-fusion) by ELISA. The huzvegf3-2 peptide-specific antibodies had an LLD of 1 ng/ml by ELISA. The huzvegf3-3 peptide-specific antibodies had an LLD of 50 pg/ml by ELISA and recognized recombinant protein by Western Blot analysis. The huzvegf34 peptide-specific antibodies had an LLD of 50 pg/ml by ELISA and recognized recombinant protein by Western Blot analysis.

Example 8

Mouse hybridomas producing monoclonal antibodies (MAbs) specific for recombinant human zvegf3 growth factor domain (GFD) protein were generated using purified, untagged, recombinant human zvegf3 GFD produced in BHK cells (huzvegf3-GFD-BHK). Ten BALB/c mice were each injected IP on day 1 with 20 $\mu$g of huzvegf3-GFD-BHK mixed 1:1 (v/v) in complete Freund's adjuvant. Each mouse was subsequently injected IP with 10 $\mu$g of huzvegf3-GFD-BHK mixed 1:1 in incomplete Freund's adjuvant on days 15, 29, 41, 57, 71, 89 and 115. On day 118, splenocytes and lymphocytes from enlarged lymph nodes of two mice with the highest anti-huzvegf3 antibody titer (as determined in a biotinylated huzvegf3-GFD capture ELISA; see below) were fused at a 2.76:1 ratio with the X63-Ag8.653 mouse myeloma cell line (Kearney et al., *J. Immunol.* 123:1548–1550, 1979) essentially as disclosed by Lane (J. Immunol. Methods 81:223–228, 1985). The fusion mixture was plated into 24 96-well plates at an average density of $1.2\times10^5$ total cells/well in Iscove's modified Dulbecco's medium (IMDM; Life Technologies, Inc., Gaithersburg, Md.) containing 10% fetal clone I serum (HyClone Laboratories, Inc., Logan, Utah), 10% hybridoma cloning supplement (BM Condimed® H1; Roche Diagnostics Corp., Indianapolis, Ind.), 2 mM L-glutamine (Life Technologies, Inc.), 100 U/mL penicillin G sodium (Life Technologies, Inc.), and 100 $\mu$g/mL streptomycin sulfate (Life Technologies, Inc.). Wells were fed on days 4 and 7 by aspiration and replacement of approximately three-fourths of the media contents in each well. This fusion was designated HH1.

Anti-huzvegf3 mAbs of the IgG class were detected on days 9/10 post-fusion using a biotinylated huvegf3-GFD capture ELISA. Wells of plates (Immulon®II; Dynex Technologies, Chantilly, Va.) were coated with 1 $\mu$g/mL of goat anti-mouse IgG (obtained from Kirkegaard & Perry Laboratories, Gaithersburg, Md.) in 0.05 M carbonate/bicarbonate buffer (Sigma, St. Louis, Mo.), 50 $\mu$L/well. Plates were incubated at 4° C. overnight, then washed three times with phosphate buffered saline containing 0.05% polyoxyethylenesorbitan monolaurate (Tween 20) (PBST) to remove unbound antibody. Wells were blocked with PBST containing 1% (w/v) bovine serum albumin (Sigma) (PTB buffer), 200 $\mu$L/well, for 1 hour at room temperature (RT), then washed as above. Culture supernatants from the fusion plates were replica-plated onto antibody-coated plates, 100 $\mu$L/well, and incubated at RT for 1 hour. Human zvegf310 GFD protein was biotinylated with sulfo-NHS-LC-biotin (Pierce Chemical Company, Rockford, Ill.) according to the manufacturer's instructions for 45 minutes at RT. The reaction was stopped with 2M glycine. Biotinylated protein was diluted to 1 µg/mL in PTB buffer. The plates were washed four times with PBST, biotinylated huzvegf3-GFD was added at 100 µL/well, and the plates were incubated at RT for 1 hour. The plates were then washed four times with PBST, and HRP-conjugated streptavidin (Pierce Chemical Company) was diluted to 0.5 µg/mL in PTB buffer and added 100 to the plates at µL/well. The plates were incubated at RT for 1 hour, then washed five times with PBST. TMB substrate (EIA chromagen, Cat. # R6R; Genetic Systems Corp.) was diluted 1:100 in substrate buffer (Genetic Systems Corp.) and added to the plates at 100 µL/well. The plates were incubated 10–15 minutes at RT in the dark. Color development was stopped by the addition of 100 µL/well of 1N $H_2SO_4$. Optical density was read on an ELISA plate reader (Molecular Devices, Sunnyvale, Calif.) at wavelengths 450 nm (L1) and 650 nm (L2). Final OD measurement was determined by the formula L1–L2.

78 master wells contained antibody that was capable of capturing biotinylated huzvegf3-GFD. These master wells were expanded for hybridoma cryopreservation and additional supernatant generation. ELISA analysis of the expanded master well supernatants demonstrated that 27 of the original 78 master wells retained antibody specific for huzvegf3-GFD, with 20 of 27 possessing significant reactivity with the antigen.

Six of the designated master wells were cloned by limiting dilution at a density of less than one cell per well. Monoclonality was assessed by microscopic examination of wells for a single focus of cell growth. Clones were tested for specific antibody by the same assay used in the master screen. Five to six of the strongest clones were briefly expanded. Supernatants from these clones was then serially diluted and tested by ELISA to identify the three best antibody-producing clones. Upon verification, the best clone from each master well was subsequently recloned and assayed as described above.

Six of the highest titered second round clones were adapted to growth in fusion/cloning medium minus the addition of hybridoma cloning supplement. Each of the clones was subsequently adapted to growth in a production medium formulation consisting essentially of Dulbecco's modified Eagle's medium+2.5% fetal clone I serum and various supplements. Supernatants were again serially diluted and tested by ELISA on huzvegf3-GFD to identify the highest titered and next highest titered clones (designated the primary and secondary clones, respectively). MAb produced by each set of clones was then evaluated for IgG subclass using the Mouse Hybridoma Subtyping Kit (Cat. #1183117; Roche Diagnostics Corp.). Clones HH1-24, 40, -57 and -76 were all found to produce an $IgG_1$ antibody. Clones HH1-58 and -78 produced an $IgG_{2b}$ antibody. All antibodies possessed a K light chain.

Example 9

Recombinant zvegf3 was analyzed for mitogenic activity on rat stellate cells (Greenwel et al., *Laboratory Invest.* 65:644, 1991; Greenwel et al., *Laboratory Invest.* 69:210, 1993). Stellate cells were plated at a density of 2,000 cells/well in 96-well culture plates and grown for approximately 72 hours in DMEM containing 10% fetal calf serum at 37° C. Cells were quiesced by incubating them for 20 hours in serum-free DMEM/Ham's F-12 medium containing insulin (5 µg/ml), transferrin (20 µl/ml), and selenium (16 pg/ml) (ITS). At the time of the assay, the medium was removed, and test samples were added to the wells in triplicate. Test samples consisted of either conditioned media (CM) from adenovirally-infected HaCaT human keratinocyte cells (Boukamp et al., *J. Cell. Biol.* 106:761–771, 1988) expressing full-length zvegf3, purified growth factor domain expressed in BHK cells, or control media from cells infected with parental adenovirus (Zpar) containing an expression unit for green fluorescent protein. The CM was concentrated 10-fold using a 15-ml centrifugal filter device with a 10K membrane filter (Ultrafree®; Millipore Corp., Bedford, Mass.), then diluted back to 3× with ITS medium and added to the cells. Purified protein in a buffer containing 0.1% BSA was serially diluted into ITS medium at concentrations of 1 µg/ml to 1 ng/ml and added to the test plate. A control buffer of 0.1% BSA was diluted identically to the highest concentration of zvegf3 protein and added to the plate. For measurement of [$^3$H]thymidine incorporation, 20 µl of a 50 µCi/ml stock in DMEM was added directly to the cells, for a final activity of 1 µCi/well. After another 24-hour incubation, mitogenic activity was assessed by measuring the uptake of [$^3$H]thymidine. Media were removed, and cells were incubated with 0.1 ml of trypsin until cells detached. Cells were harvested onto 96-well filter plates using a sample harvester (FilterMate™ harvester; Packard Instrument Co., Meriden, Conn.). The plates were then dried at 65° C. for 15 minutes, sealed after adding 40 µl/well scintillation cocktail (Microscint™ O; Packard Instrument Co.) and counted on a microplate scintillation counter (Topcount®; Packard Instrument Co.).

Results, presented in Table 3, demonstrated that zvegf3 CM bad approximately 4.4-fold higher mitogenic activity on stellate cells over control CM, and purified protein at 100 ng/ml caused a maximal 14-fold increase in [$^3$H]thymidine incorporation over the buffer control.

TABLE 3

| Sample | CPM Incorporated | |
|---|---|---|
| | Mean | St. dev. |
| zvegf3 (2x CM) | 42489 | 1306 |
| Zpar (2x CM) | 9629 | 540 |
| zvegf3 GF domain, 100 ng/ml | 77540 | 4142 |
| zvegf3 GF domain, 33.3 ng/ml | 74466 | 18142 |
| zvegf3 GF domain, 11.1 ng/ml | 52462 | 6239 |
| zvegf3 GF domain, 3.7 ng/ml | 15128 | 4989 |
| Buffer control | 5618 | 573 |
| PDGF-BB 20 ng/ml | 19741 | 2075 |
| PDGF-AA 20 ng/ml | 33133 | 3325 |
| Media alone (basal response) | 6765 | 226 |

Example 10

Northern blot analysis was performed on 2 µg samples of poly(A)+ RNA from five mouse prostate cell lines (designated Jakotay, Nelix, Paris, Torres, and Tuvak). Total RNA from mouse and rat liver were used as controls (20 µg each). An approximately 680-bp DNA probe was generated by PCR using oligonucleotide primers ZC21,222 (SEQ ID NO:9) and ZC21,224 (SEQ ID NO:10) and a mouse zvegf3 full-length cDNA clone as a template. The DNA probe was purified by conventional procedures using a commercially available kit (QIAquick™ Gel Extraction Kit; Qiagen, Inc., Valencia, Calif.). The probe was radioactively labeled with $^{32}$P using a commercially available kit (Rediprime™ II DNA Labeling system; Amersham, Arlington Heights, Ill.) according to the manufacturer's specifications. The probe was purified using a push column (NucTrap® column; Stratagene, La Jolla, Calif.; see U.S. Pat. No. 5,336,412). A commercially available hybridization solution (ExpressHyb™ Hybridization Solution; Clontech Laboratories, Inc., Palo Alto, Calif.) was used for the blots. Hybridization took place overnight at 65° C. The blots were then washed four times in 2×SCC and 0.1% SDS at room temperature, followed by two washes in 0.1×SSC and 0.1% SDS at 55° C. One transcript size was detected at approximately 4 kb in Jakotay, Nelix, Paris and Tuvak cell lines. Signal intensity was highest for Jakotay, then Nelix and Tuvak.

Example 11

Recombinant human zvegf3 GFD produced in BHK cells was assayed for growth factor activity using an osteoblast cell line containing a luciferase reporter gene construct. CCC4 cells (derived from p53 knock-out mice) transfected with the reporter construct were plated in 96-well plates (BioCoat™; Becton Dickinson, Franklin Lakes, N.J.) at $1 \times 10^4$ cells/well in 1% FBS alpha MEM (JRH Biosciences, Lexena, Kans.) containing L-Glutamine and sodium pyruvate (Life Technologies, Inc.). The cells were cultured for 24 hours, the medium was removed, and the wells were washed twice with wash buffer (1% BSA in PBS), 100 µl/well at 37° C. Zvegf3, PDGF-AA, and PDGF-BB were diluted in assay medium (alpha MEM containing 1% BSA, 10 mM Hepes, L-Glutamate, and sodium pyruvate), and 100-1 samples were added to the wells. The plates were incubated 4 hours at 37° C., then the wells were washed with wash buffer. Lysis reagent (Cell Culture Lysis Reagent; Promega Corporation, Madison, Wis.) was diluted 1:5 in water, and 25 µl was added to each well. The plates were incubated 10 minutes at room temperature, then transferred to −20° C. Luciferase substrate (Luciferase Assay System; Promega Corporation) was diluted 1:1 with assay medium and added to the wells. The plates were read on a luminometer. Results, shown in Table 4, indicted that all three growth factors exhibited mitogenic activity on the CCC4 cells.

TABLE 4

| Concentration | Activity (Luminometer Units) | | |
|---|---|---|---|
| (ng/ml) | Zvegf3 | PDGF-BB | PDGF-AA |
| 0 | 3.5 | 3.1 | 3.2 |
| 0.4 | 5.2 | 7.7 | 8.4 |
| 0.8 | 5.6 | 10.7 | 9.5 |
| 1.5 | 7.6 | 14 | 9.4 |
| 3.1 | 10.6 | 19.9 | 11.4 |
| 6.2 | 12.5 | 25.1 | 12 |
| 12.5 | 14.2 | 26.1 | 12.3 |
| 25 | 16 | 25.7 | 11.9 |
| 50 | 19.4 | 25.8 | 12.6 |
| 100 | 20.6 | 23.8 | 14 |

Example 12

A study was undertaken to test whether adenovirally delivered zvegf3 stimulated cell proliferation as determined by incorporation of bromodeoxyuridine (BrdU) into tissues. Mice (male, C57B1, 7 weeks old) were divided into three groups. On 110 day 0, parental or zvegf3 adenovirus was administered to the first (n=11) and second (n=12) groups, respectively, via the tail vein, with each mouse receiving a dose of —$1 \times 10^{11}$ particles in ~0.1 ml volume. The third group (n=8) received no treatment. Each mouse was given two intraperitoneal doses of 3 mg of freshly made BrdU solution at approximately 24 and 12 hours prior to sacrifice. On days 2, 4, 6, 8, and 10, two mice from each treatment group and one or two untreated mice were sacrificed, and tissues and blood were harvested. Samples were analyzed for complete blood count (CBC) and serum chemistry, and slides were prepared for manual differential blood and marrow progenitor cell analysis. One femur, lung, heart, thymus, liver, kidney, spleen, pancreas, duodenum, and mesenteric lymph nodes were submitted for standard histology and assessment of BrdU incorporation. The lining of the duodenum served as the control tissue for BrdU incorporation.

In addition, two mice that received approximately half the dose of zvegf3 adenovirus particles and one mouse that received the full dose of parental adenovirus were sacrificed and analyzed as described above on day 16.

A piece of liver from each mouse was saved for mRNA assay of adenovirus protein to examine the time course of expression of the adenovirus preparations.

Beginning on day 6, most of the animals treated with either adenovirus had visibly enlarged livers and spleens compared to the untreated mice. The livers of the zvegf3 adenovirus-treated mice tended to look more pale than animals treated with the parental virus. Proliferation of sinusoidal cells was observed in liver. Visual inspection suggested that these cells were stellate cells and/or fibroblasts. Spleen color was the same in both groups. Most of the animals that received the zvegf3 adenovirus had paler femur shafts, with the marrow lighter in color.

Peripheral blood CBCs showed a possible difference in platelet counts, but not in RBC or WBC counts between zvegf3 and parental virus-treated animals. In comparison to the untreated and parental virus-treated groups, the zvegf3 group had lower platelet counts on days 2, 4, 6, and 8, but not on day 10. The mean platelet volume (average size of individual platelets) in the zvegf3 group also tended to be greater, consistent with a relative increase in the larger, immature platelet population.

BrdU labeling showed increased cell proliferation in kidney, mainly in the medulla and to a lesser extent in the cortex. Proliferating cells appeared to be interstitial cells, which may have included fibroblasts and/or mesangial cells.

Example 13

Human zvegf3 growth factor domain protein produced in BHK cells was tested for the ability to stimulate production of TGF-β in stellate cells. Rat hepatic stellate cells (obtained from Dr. Nelson Fausto, University of Washington) were plated in 48-well tissue culture clusters (Costar®; Corning, Corning, N.Y.) in DMEM growth medium (Life Technologies, Inc.) supplemented with pyruvate and 10% serum (HyClone Laboratories, Inc.). At confluence, the medium was changed to serum-free medium by substituting 0.1% BSA (Fraction V; Sigma, St. Louis, Mo.) for serum. 48 hours later, the medium was changed, replaced with the same serum-free medium, and the zvegf3 GFD protein was added at 100 ng/ml in the wells. 48 hours later, conditioned media were collected and spun down to get rid of any floating cells or debris. Total TGF-β1 levels were determined in these media using a commercially available ELISA kit (R&D Systems, St Paul, Minn.). Stimulation of stellate cells with 100 ng/ml zvegf3 GFD resulted in an approximately 5-fold increase in the production of TGF-β compared to a BSA control.

Example 14

Recombinant human zvegf3 GFD was analyzed for mitogenic activity on human mesangial cells (Clonetics, San Diego, Calif.). Mesangial cells were plated at a density of 2,000 cells/well in 96-well culture plates and grown for approximately 72 hours in DMEM containing 10% fetal calf serum at 37° C. Cells were quiesced by incubating them for 20 hours in serum-free DMEM/Ham's F-12 medium containing insulin (5 μg/ml), transferrin (20 μg/ml), and selenium (16 pg/ml) (ITS). At the time of the assay, the medium was removed, and test samples were added to the wells in triplicate. Test samples consisted of purified zvegf3 GFD at 3, 10, 30 and 100 ng/ml, and PDGF-AA, PDGF-AB and PDGF-BB at 30 ng/ml in a buffer containing 0.1% BSA. Samples were serially diluted into ITS medium and added to the test plate. A control buffer of 0.1% BSA was diluted identically to the highest concentration of zvegf3 protein and added to the plate. 10% fetal bovine serum (FBS) was used as a positive control. For measurement of [$^3$H]thymidine incorporation, 20 μl of a 50 μCi/ml stock in DMEM was added directly to the cells, for a final activity of 1 μCi/well. After another 24-hour incubation, mitogenic activity was assessed by measuring the uptake of [$^3$H]thymidine. Media were removed, and cells were incubated with 0.1 ml of trypsin until cells detached. Cells were harvested onto 96-well filter plates using a sample harvester (FilterMate™ harvester; Packard Instrument Co., Meriden, Conn.). The plates were then dried at 65° C. for 15 minutes, sealed after adding 40 μl/well scintillation cocktail (Microscint™ 0; Packard Instrument Co.), and counted on a microplate scintillation counter (Topcount®; Packard Instrument Co.). Results, shown in Table 5, demonstrated that zvegf3 GFD had approximately 3-fold higher mitogenic activity cells over PDGF-AA and comparable activity to PDGF-AB and PDGF-BB at 30 ng/ml on mesangial cells.

TABLE 5

| Sample | CPM [$^3$H] Thymidine Incorporated | |
|---|---|---|
| | Mean | St. dev. |
| PDGF-AA, 30 ng/ml | 492 | 120 |
| PDGF-AB, 30 ng/ml | 1554 | 114 |
| PDGF-BB, 30 ng/ml | 1852 | 464 |
| Zvegf3 GFD, 3 ng/ml | 1321 | 91 |
| Zvegf3 GFD, 10 ng/ml | 1615 | 325 |
| Zvegf3 GFD, 30 ng/ml | 1545 | 237 |
| Zvegf3 GFD, 100 ng/ml | 1677 | 88 |
| 10% FBS | 1447 | 174 |
| Buffer control | 392 | 109 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. A method of reducing cell proliferation or extracellular matrix production caused by zvegf3 in a mammal comprising administering to the mammal a composition comprising a zvegf3 antagonist in combination with a pharmaceutically acceptable delivery vehicle, in an amount sufficient to reduce zvegf3 activity, wherein said zvegf3 antagonist is an antibody that specifically binds to a dimeric protein consisting of two polypeptide chains, wherein each of said polypeptide chains consists of a sequence of amino acid residues selected from the group consisting of:

residues 230–345 of SEQ ID NO:2;
residues 231–345 of SEQ ID NO:2;
residues 232–345 of SEQ ID NO:2;
residues 233–345 of SEQ ID NO:2;
residues 234–345 of SEQ ID NO:2;
residues 235–345 of SEQ ID NO:2;
residues 236–345 of SEQ ID NO:2;
residues 237–345 of SEQ ID NO:2;
residues 238–345 of SEQ ID NO:2;
residues 239–345 of SEQ ID NO:2; and
residues 240–345 of SEQ ID NO:2,
whereby administration of the composition to the mammal results in reduction of cell proliferation or extracellular matrix production caused by zvegf3.

2. The method of claim 1 wherein proliferation of mesangial, endothelial, smooth muscle, fibroblast, osteoblast, osteoclast, stellate, or interstitial cells is reduced.

3. The method of claim 1 wherein extracellular matrix production is reduced.

4. The method of claim 1 wherein the mammal is suffering from a fibroproliferative disorder of the liver.

5. The method of claim 1 wherein the mammal is suffering from a fibroproliferative disorder of the kidney.

6. The method of claim 1 wherein the mammal is suffering from a fibroproliferative disorder of bone.

7. The method of claim 1 wherein the antibody is a monoclonal antibody.

8. The method of claim 1 wherein the antibody is a single-chain antibody.

9. The method of claim 1 wherein the antibody is a humanized antibody.

10. A method of treating reducing fibrosis caused by zvegf3 in a mammal comprising administering to the mammal a composition comprising a zvegf3 antagonist in combination with a pharmaceutically acceptable delivery vehicle, in an amount sufficient to reduce zvegf3 activity, wherein the zvegf3 antagonist is an antibody that specifically binds to a dimeric protein having consisting of two polypeptide chains, wherein each of said polypeptide chains consists of a sequence of amino acid residues selected from the group consisting of:

residues 230–345 of SEQ ID NO:2;
residues 231–345 of SEQ ID NO:2;
residues 232–345 of SEQ ID NO:2;
residues 233–345 of SEQ ID NO:2;
residues 234–345 of SEQ ID NO:2;
residues 235–345 of SEQ ID NO:2;
residues 236–345 of SEQ ID NO:2;
residues 237–345 of SEQ ID NO:2;
residues 238–345 of SEQ ID NO:2;
residues 239–345 of SEQ ID NO:2; and
residues 240–345 of SEQ ID NO:2,
whereby administration of the composition to the mammal results in treatment of fibrosis caused by zvegf3.

11. The method of claim 10 wherein the fibrosis is liver fibrosis.

12. The method of claim 10 wherein the fibrosis is kidney fibrosis.

13. The method of claim 10 wherein the antibody is a monoclonal antibody.

14. The method of claim 10 wherein the antibody is a single-chain antibody.

15. The method of claim 10 wherein the antibody is a humanized antibody.

16. A method of reducing stellate cell activation caused by zvegf3 in a mammal comprising administering to the mammal a composition comprising a zvegf3 antagonist in combination with a pharmaceutically acceptable delivery vehicle, in an amount sufficient to reduce zvegf3 activity, wherein the zvegf3 antagonist is an antibody that specifically binds to a dimeric protein consisting of two polypeptide chains, wherein each of said polypeptide chains consists of a sequence of amino acid residues selected from the group consisting of:

residues 230–345 of SEQ ID NO:2;
residues 231–345 of SEQ ID NO:2;
residues 232–345 of SEQ ID NO:2;
residues 233–345 of SEQ ID NO:2;
residues 234–345 of SEQ ID NO:2;
residues 235–345 of SEQ ID NO:2;
residues 236–345 of SEQ ID NO:2;
residues 237–345 of SEQ ID NO:2;
residues 238–345 of SEQ ID NO:2;
residues 239–345 of SEQ ID NO:2; and
residues 240–345 of SEQ ID NO:2, whereby administration of the composition to the mammal results in reduction of stellate cell activation caused by zvegf3.

17. The method of claim 16 wherein the stellate cells are liver stellate cells.

18. The method of claim 16 wherein the antibody is a monoclonal antibody.

19. The method of claim 16 wherein the antibody is a single-chain antibody.

20. The method of claim 16 wherein the antibody is a humanized antibody.

* * * * *